(12) United States Patent
Moore et al.

(10) Patent No.: US 11,045,323 B2
(45) Date of Patent: Jun. 29, 2021

(54) ALIGNMENT GUIDE

(71) Applicant: DEPUY IRELAND UNLIMITED COMPANY, Ringaskiddy (IE)

(72) Inventors: Gary Moore, Wetherby (GB); Alec Birkbeck, Leeds (GB); Christopher Hunt, Leeds (GB); Richard Patnelli, Leeds (GB); David Horne, Leeds (GB); Henry Prout, Leeds (GB)

(73) Assignee: DePuy Ireland Unlimited Company, Ringaskiddy (IE)

( * ) Notice: Subject to any disclaimer, the term of this patent is extended or adjusted under 35 U.S.C. 154(b) by 232 days.

(21) Appl. No.: 15/751,911

(22) PCT Filed: Aug. 10, 2016

(86) PCT No.: PCT/EP2016/069064
§ 371 (c)(1),
(2) Date: Feb. 12, 2018

(87) PCT Pub. No.: WO2017/029173
PCT Pub. Date: Feb. 23, 2017

(65) Prior Publication Data
US 2018/0235764 A1  Aug. 23, 2018

(30) Foreign Application Priority Data

Aug. 19, 2015 (GB) ....................... 1514727
Jul. 18, 2016 (GB) ....................... 1612399

(51) Int. Cl.
*A61F 2/40* (2006.01)
*A61F 2/46* (2006.01)
(Continued)

(52) U.S. Cl.
CPC .......... *A61F 2/4014* (2013.01); *A61F 2/4637* (2013.01); *A61F 2002/30332* (2013.01);
(Continued)

(58) Field of Classification Search
CPC ................ A61F 2/4014; A61F 2/4637; A61F 2002/30332; A61F 2002/365; A61F 2002/4037
See application file for complete search history.

(56) References Cited

U.S. PATENT DOCUMENTS 4,676,798 A * 6/1987 Noiles .................. A61F 2/32
 623/22.18
4,865,609 A    9/1989 Roche
(Continued)

FOREIGN PATENT DOCUMENTS

EP      1169981 A1    1/2002
EP      1776937 A1    4/2007
JP     H02-200260    8/1990

OTHER PUBLICATIONS

Chinese Exam Report and Search Report dated Aug. 5, 2019 (English translation).

(Continued)

*Primary Examiner* — Jerrah Edwards
*Assistant Examiner* — Christine L Nelson
(74) *Attorney, Agent, or Firm* — Cynthia K. Barnett

(57) ABSTRACT

An orthopaedic joint prosthesis assembly includes a head part of an orthopaedic joint prosthesis component and an alignment guide. The head part has a spherical hearing surface for articulation with a corresponding joint surface, and an assembly surface having a first bore formed in it for receiving a spigot on another part of the orthopaedic joint prosthesis. The bore has a first axis that extends perpendicular to the assembly surface. The alignment guide has an axial portion defining a second axis and an arm extending from the axial portion. The arm includes a distal portion which is configured to engage the assembly surface, with the axial portion being arranged to engage the bearing surface of the head part when the head part is mounted within the guide such that an impaction force applied along the second axis is directed along the first axis.

11 Claims, 17 Drawing Sheets

(51) Int. Cl.
*A61F 2/30* (2006.01)
*A61F 2/36* (2006.01)

(52) U.S. Cl.
CPC . *A61F 2002/365* (2013.01); *A61F 2002/4037* (2013.01); *A61F 2002/4627* (2013.01); *A61F 2002/4628* (2013.01); *A61F 2002/4681* (2013.01)

(56) References Cited

U.S. PATENT DOCUMENTS

| | | | |
|---|---|---|---|
| 5,133,765 A * | 7/1992 | Cuilleron | A61F 2/0095 206/363 |
| 5,735,855 A | 4/1998 | Bradley | |
| 6,517,582 B2 | 2/2003 | Willi et al. | |
| 6,585,771 B1 | 7/2003 | Buttermilch | |
| 7,708,739 B2 | 5/2010 | Kilburn | |
| 2003/0229357 A1 | 12/2003 | Dye | |
| 2012/0143200 A1 | 6/2012 | Honiball | |

OTHER PUBLICATIONS

JP Office Action dated Aug. 4, 2020—English translation.
PCT Intl Search Report and Written Opinion for PCT/EP2016/069064 dated Dec. 12, 2016. 12 pages.
GB1514727.5 Search Report dated Feb. 18, 2016, 4 pages.
Abstract—English translation of EP1190687A1.
European Search Report issued in divisional—EP20150477.6 dated May 18, 2020.
English Translation of Abstract for DE202012102017.

\* cited by examiner

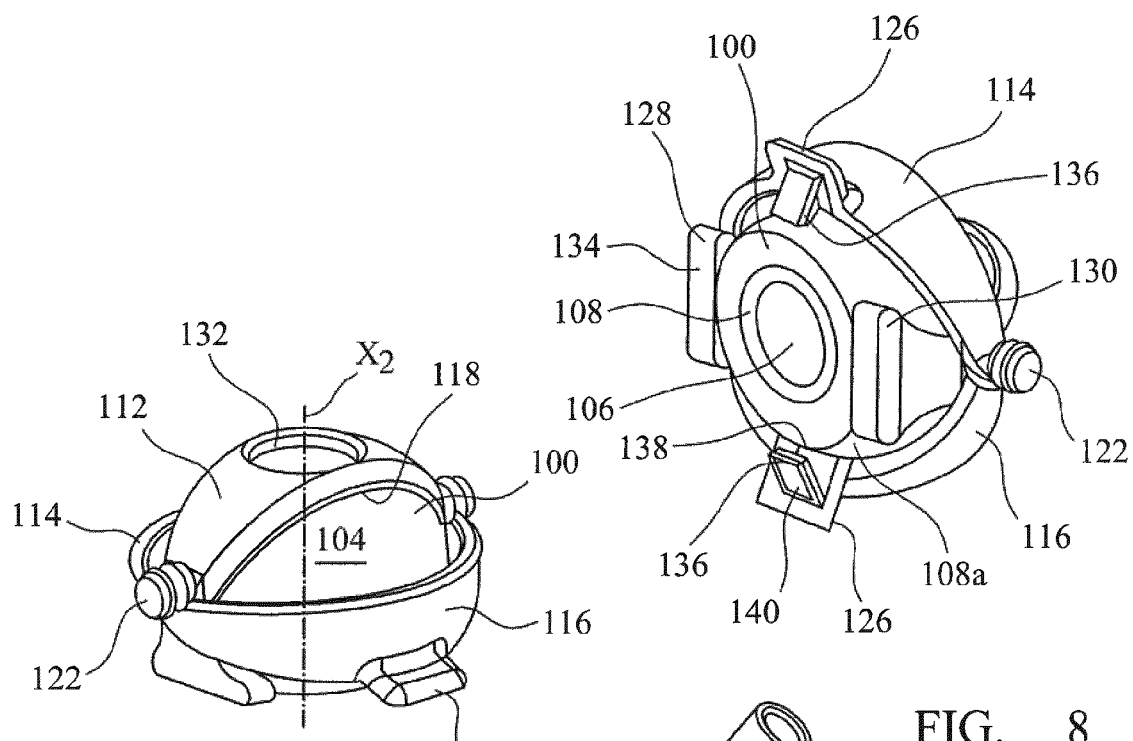
FIG. 7
FIG. 8
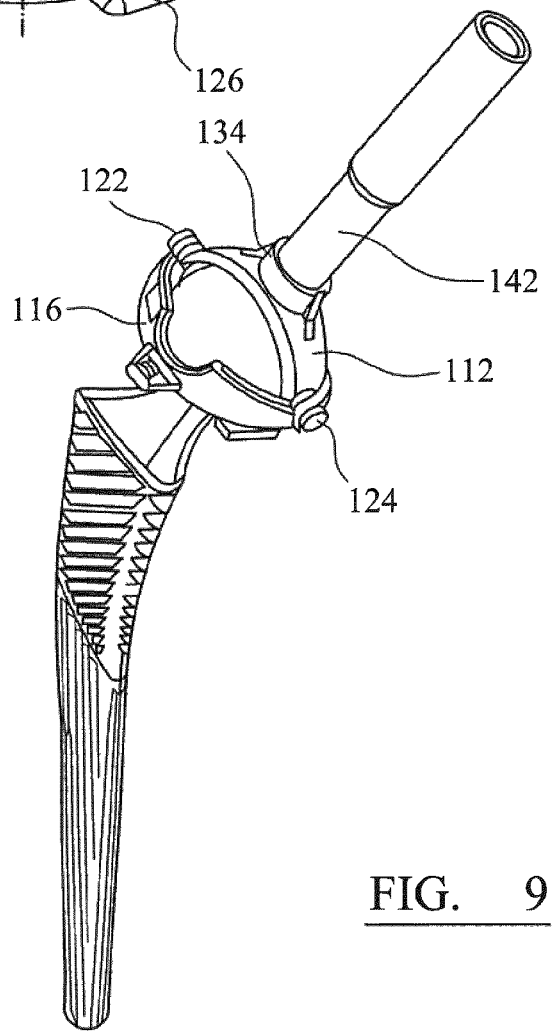
FIG. 9

Detail G

Detail G

ALIGNMENT GUIDE

CROSS REFERENCE TO RELATED APPLICATIONS

This application is the national stage of PCT Application No. PCT/EP2016/069064, filed Aug. 10, 2016, which claims priority from Great Britain Application No. 1514727.5, filed Aug. 19, 2015 and Great Britain Application No. 1612399.4, filed Jul. 18, 2016, the entire disclosures of which are hereby incorporated in their entirety.

This invention relates an orthopaedic joint prosthesis assembly which includes a head part of a joint prosthesis component and alignment guide.

Many orthopaedic joint prosthesis components are modular. A modular construction allows components to be assembled to meet particular requirements, for example to take account of anatomical variations between patients or surgeon preference. Examples of modular orthopaedic joint prosthesis components include femoral components of hip joint prostheses and humeral components of shoulder joint prostheses. Each of these comprises a stem part which is fitted in the intramedullary cavity of the bone (femur or humerus) and a head part. The head part has a bearing surface for articulation with a corresponding joint surface which can be provided by a mating joint prosthesis component (an acetabular component or a glenoid component) or by the patient's natural tissue. The head part has an assembly surface opposite to the bearing surface where the head part is connected to the stem part.

It is common to fasten modular parts of a joint prosthesis component to one another by means of a self-locking taper in which a tapered spigot (a term used to refer to a short projection on one component which fits into a bore in another component, in order to fasten the components together) on one part is received in a correspondingly tapered bore in the other part. An example of such a self-locking taper is a Morse taper in which the angle between the tapered surface of each of the spigot and the bore and the longitudinal axis of the spigot and the bore (when the part is viewed in cross-section) is about 1.4° to about 1.5°.

The security of a joint between two taper locked parts depends on the force that is applied to the parts when they are assembled. Sufficient force should be applied to ensure proper engagement of the surfaces of the spigot and the bore. However, it can sometimes be important to ensure that the applied force does not exceed a maximum limit, for example to avoid damage to a patient's bone tissue if the parts are being assembled with one implanted in the patient's bone, or to avoid damage to the parts of the component.

EP-A-1707160 discloses a device for applying an assembly force to parts of an orthopaedic joint prosthesis component. The device includes a hollow housing and an impacting rod which extends from the housing with a tip for contacting one of the parts of the prosthesis component. The housing contains a piston which can slide in the housing. A spring is located between an end of the piston and a closed end of the housing. Use of the device involves compressing the spring by forcing the piston towards the closed end of the housing and then releasing the piston so that it can slide within the housing, acted on by the spring as it relaxes.

The present invention provides an orthopaedic joint prosthesis assembly that includes an alignment guide which can engage an assembly surface of the head part of an orthopaedic joint prosthesis, opposite its bearing surface, so that an assembly force is applied to the parts of the prosthesis component can be directed along a first axis defined by the bore in the head part through use of the assembly surface as a reference for the alignment guide.

The invention therefore provides an orthopaedic joint prosthesis assembly which comprises:

a. a head part of an orthopaedic joint prosthesis component, which has a spherical bearing surface for articulation with a corresponding joint surface, and an assembly surface having a first bore formed in it for receiving a spigot on another part of the orthopaedic joint prosthesis, said bore having a first axis that extends perpendicular to the assembly surface, and in which there is a discontinuity at an interface between the bearing surface and the assembly surface, the said assembly surface being arranged on a plane which is parallel to, or contains, a plane which is defined by the opening to the bore in the head part when the head part is viewed from one side in cross-section, and b. an alignment guide comprising an axial portion and an arm extending from the axial portion, the arm including a distal portion and a proximal portion, the distal portion being configured to engage the assembly surface of the head part, the axial portion defining a second axis and being arranged to engage the bearing surface of the head part, directly or indirectly, when the head part is mounted within the guide, with the second axis coincident with the first axis, such when an impaction force is applied along the second axis the force is directed along the first axis.

The orthopaedic joint prosthesis assembly of the invention can be used in a surgical procedure to implant an orthopaedic joint prosthesis component which includes a head part and another part. Frequently, the other part will be a stem part which can be fitted in the intramedullary cavity of a patient's long bone. The invention is therefore useful in a surgical procedure to implant a femoral component of a hip joint prosthesis in which the bore in the assembly surface of the head part receives a spigot on the stem part which is intended to be fitted into the intramedullary cavity of the patient's femur. The invention is also useful in a surgical procedure to implant a humeral component of a shoulder joint prosthesis in which the bore in the assembly surface of the head part receives a spigot on the stem part which is intended to be fitted into the intramedullary cavity of the patient's humerus.

The alignment guide will be dimensioned to suit the dimensions of the prosthesis head part which is to be manipulated. The transverse dimension (which will be the diameter when the head part is configured with a spherical bearing surface) of the head part of a femoral component of a hip joint prosthesis will frequently be at least about 15 mm. It could be up to about 50 mm. The transverse dimension of the head part of a humeral component of a shoulder joint prosthesis will frequently be at least about 25 mm. It could be up to about 60 mm.

Each of the bearing surface and the assembly surface of the head part of the prosthesis component of the joint prosthesis assembly can be cylindrically symmetrical, with the axis of the bore is coincident with the axis of symmetry of the bearing surface. The term "cylindrically symmetrical" is used to refer to a shape which is rotationally symmetrical of infinite order. However, the joint prosthesis assembly can include a head part in which one or both of the bearing surface and the assembly surface is not cylindrically symmetrical. For example, an assembly surface might be generally circular in outline with the bore in the assembly surface being offset relative to the centre of the circular outline. A bearing surface might be defined by the surface of part of a sphere. However, a bearing surface might be curved (convex or concave) but not necessarily part spherical.

The bearing surface on the head part can be convex. This will generally be the case when the prosthesis component is a femoral component of a hip joint prosthesis. It will also generally be the case when the prosthesis component is a humeral component of an anatomic shoulder joint prosthesis.

The bearing surface on the head part can be concave. This will generally be the case when the prosthesis component is a humeral component of a reverse shoulder joint prosthesis.

The axis which is defined by the bore in the head part extends perpendicular to the assembly surface. The assembly surface is at one end of the axis and the centre of the bearing surface is at the opposite end of the axis. The assembly surface surrounds the bore. The assembly surface will generally be contained in a plane which is perpendicular to the axis defined by the bore in the head part. The assembly surface is arranged on a plane which is parallel to and/or contains the opening to the bore in the head part. The assembly surface can be shaped as a narrow ridge. The assembly surface can be provided in the form of one or more generally flat portions which are defined by a straight lines when the head part is viewed in cross-section. At least one flat portion can be planar, containing or parallel to the plane of the opening to the bore in the head part. The assembly surface can includes a chamfer portion extending around the head part which is inclined to the plane which is defined by the opening to the bore in the head part when the head part is viewed from one side in cross-section. The assembly surface can include a flat planar portion which lies in the plane defined by the opening to the bore in the head part, and a chamfer portion between the flat planar portion and the bearing surface of the head part. The assembly surface can include a portion which is curved when the head part is viewed from one side in cross-section. For example, the assembly surface can include a portion which is convex and/or a portion which is concave. Such portions (flat, chamfer and curved) can extend annularly around the opening to the bore in the head part.

The assembly surface will be capable of being distinguished from the adjacent bearing surface. The bearing surface itself will be free of discontinuities which might interfere with smooth articulation of the head part with a corresponding joint surface as is the case when, for example, the bearing surface is the surface of part of a sphere. It will frequently be the case that there will be a discontinuity at the interface between the bearing and assembly surfaces, for example through a change in curvature which gives rise to a discernible ridge. The bearing surface will frequently be polished to a lower surface roughness than the assembly surface. Appropriate surface roughness levels for the bearing surface of an orthopaedic joint prosthesis component are well established. The assembly surface might have markings on it, for example to identify the component (for example its size).

The orthopaedic joint prosthesis assembly can include a part of the orthopaedic joint prosthesis having a spigot which can be received in the bore in the assembly surface of the head part. An example of such a part is a stem part of an orthopaedic joint prosthesis which can be fitted at least partially into the intramedullary cavity of a patient's bone.

In the constructions of the orthopaedic joint prosthesis assembly in which the axial portion of the alignment guide is arranged to directly contact the bearing surface of the head part, the axial portion includes a bearing surface seating member.

Optionally, the axial portion is a shaft having a distal end and a proximal end. A longitudinal axis extends between the distal end and the proximal end of the shaft. This longitudinal axis defines the second axis. The distal end of the shaft includes a bearing surface seating member configured to directly engage the bearing surface of the prosthesis component head part. The second axis extends centrally through the bearing surface seating member. An impaction force applied directly to the proximal end of the shaft is therefore aligned with the first axis that is defined by the bore in the head part.

In some constructions, the shaft includes a blind-bore extending longitudinally from the proximal end towards the distal end. The blind-bore is dimensioned to receive an impaction tool, such as an impaction rod (through which an impaction force can be applied to the prosthesis component head part). The impaction rod has a longitudinal axis. When the impaction rod is received within the blind bore the longitudinal axis of the impaction rod is coincident with the second axis. An impaction force can be applied to head part of the prosthesis component by applying an impaction force to the proximal end of the impaction rod. An impaction force applied indirectly to the shaft in this manner is therefore aligned with the first axis that is defined by the bore in the head part.

Optionally, the axial portion is a hemi-spherical hub having a convex outer surface and a concave inner surface. The convex outer surface has a pole. An axis extends through the pole. This pole axis defines the second axis. The second axis is coincident with the first axis as defined by the bore in the head part. The concave inner surface defines a space in which a head part can be received and is configured to directly engage the bearing surface of the prosthesis component head part. An impaction rod (through which an impaction force can be applied to the prosthesis component head part) is connectable to the hub at the pole. The impaction rod has a longitudinal axis. When the impaction rod is connected to the hub at the pole, the longitudinal axis of the impaction rod is coincident with the second axis. An impaction force applied directly to the impaction rod is therefore aligned with the first axis that is defined by the bore in the head part.

The impaction rod may be connected to the hub via a socket located at the pole. The socket may be dimensioned to receive the impaction rod. In some other constructions, a sleeve can be received within the socket. The sleeve has a longitudinal axis that is coincident with the second axis. An impaction rod can extend through the sleeve component and is a sliding fit therein. The longitudinal axis of the impaction rod is also aligned with the second axis. The distal end of the impaction rod can form at least part of the bearing surface seating member. An impaction force applied via an impaction rod in this manner is therefore aligned with the first axis that is defined by the bore in the head part.

In other constructions of the orthopaedic joint prosthesis assembly in which the axial portion of the alignment guide is arranged to indirectly contact the bearing surface of the head part, the bearing surface seating member is provided on a different component of the assembly from the axial portion.

Optionally, the axial portion is a sleeve having a through bore. The sleeve has a proximal end and a distal end. A longitudinal axis extends between the distal end and the proximal end of the sleeve. This longitudinal axis defines the second axis.

A shaft is received in a sliding tight fit within the through bore of the sleeve. The shaft has a proximal end and a distal end. A longitudinal axis extends between the distal end and the proximal end of the shaft. This shaft axis is aligned with the second axis, as defined by the sleeve. The distal end of the shaft is configured as a bearing surface seating member and contacts the bearing surface of the head part when the head part is mounted within the guide.

In some constructions the shaft is an impaction tool, such as an impaction rod (through which an impaction force can be applied to the prosthesis component head part). The distal end of the impaction rod is configured as a bearing surface seating member.

In some constructions, the shaft includes a blind-bore extending from the proximal end towards the distal end. The blind-bore is configured to receive an impaction tool, such as an impaction rod. An impaction force can be applied directly to the proximal end of the shaft (for example using an instrument such as a hammer or a mallet, or an instrument which generates a controlled impaction force such as the instrument disclosed in EP-A-1707160) or indirectly via an impaction rod received within the blind-bore.

Optionally, the shaft can be translated (for example, to be driven or advanced) within the sleeve along the second axis as defined by the sleeve. For example, the sleeve and the shaft can have cooperating threads so that the shaft can be advanced through the sleeve by rotating it about its axis. For example, the shaft can have an external thread which threadingly engages an internally threaded sleeve.

This ability of the shaft to be translated allows the distance between the bearing surface seating member and the assembly surface seating member to be adjusted so that the head part of the prosthesis component can be held within the alignment guide between the two seating members. This can facilitate assembly of the head and stem (or other) parts of the prosthesis component. Rotating the shaft relative to the sleeve can increase the distance between the seating members, facilitating removal of the head part from the space between the seating members. It also enables the alignment guide to be configured for use with head parts having a range of different sizes.

It will frequently be preferred that the surface of the bearing surface seating member which contacts the bearing surface of the head part of the prosthesis component is configured so that its shape is complementary to that of the bearing surface of the head part. The bearing surface of the head part can then be a nesting fit with the contact surface of the bearing surface seating member. For example, when the bearing surface of the head part is convex, it can be appropriate for the surface of the bearing surface seating member which contacts the bearing surface to be concave. When the bearing surface of the head part is concave, it can be appropriate for the surface of the bearing surface seating member which contacts the bearing surface to be convex.

The surface of the bearing surface seating member which contacts the bearing surface of the head part of the prosthesis component should be provided by a material and finished in such a way that the risk of damage (for example, by scratching) to the bearing surface of the head part is minimized. The contact surface could be provided by a material which is softer than the material of the bearing surface. Suitable materials are known from their use in instruments which are used to contact a bearing surface of an orthopaedic joint prosthesis when assembling or implanting it. Examples of suitable materials include low and high density polyethylenes, certain silicone elastomers, and certain poly(phenyl sulphones) (such as the material sold under the trade mark Radel).

The bearing surface seating member can be configured so that it is engaged by the head part of the prosthesis component with a press fit. This can be achieved by providing the bearing surface seating member with opposing portions which extend beyond the widest point on the head part. For example, the bearing surface seating member can be made from a resiliently deformable flexible material in the form of a concave recess whose wall is required to flex outwardly in order to insert a head part into the recess. The resiliently deformable characteristics of the material of the bearing surface seating member can mean that the seating member springs back once a head part has been positioned within the alignment guide to grip the head part.

The bearing surface seating member can have a plurality of radially extending fingers (for example at least two fingers, or at least three fingers) which are shaped to fit closely against the bearing surface of the head part. The fingers can help to locate the head part centrally relative to the axial portion through which an impaction force is applied to the head part, and to position it so that it is properly aligned with the second axis as defined by the axial portion. Optionally, the fingers can be sufficiently long to extend beyond the widest point of the head part. The widest point might be the equator in the case of the head part of a femoral component of a hip joint prosthesis, or it might be the interface between the bearing and assembly surfaces of a humeral component of a shoulder joint prosthesis. It can then be preferred that the fingers are made from a resiliently flexible material. The fingers can then be help to retain the head part of the prosthesis component within the space between the bearing surface and assembly surface seating members.

Radially extending fingers can extend radially from a point which lies on the axis defined by the bore in the head part. Radially extending fingers can extend radially from a connection with the axial portion through which an impaction force is applied to the head part.

It can be convenient for the bearing surface seating member to be capable of being removably connectable to the component of the alignment guide on which it is provided. This allows a bearing surface seating member to be replaced, for example in order to select one which is adapted for use with a different head part, or because a bearing surface seating member is damaged. The components might be connected to one another by means of mating threads. For example, in constructions in which the bearing surface seating member is provided at the distal end of a shaft, the end of the shaft could have an external thread and the bearing surface seating member can have a bore formed in it with an internal thread.

The arm which extends from the axial portion of the alignment guide defines a space around at least part of the periphery of the head part of the joint prosthesis.

The alignment guide can include more than one arm, for example at least two arms, or at least three arms, or at least four arms. Optionally, there can be spaces between neighbouring arms which allow a head part mounted within the alignment guide to be viewed and inspected.

Optionally, the at least one arm is capable of being pivoted outwardly to allow access for the head part to be mounted within the alignment guide. The at least one arm can be pivotally connected to the axial portion at or towards one end. The at least one arm can be pivoted outwardly to allow access for the head part to be mounted within the alignment guide. The at least one arm can then be pivoted inwardly to position the assembly surface seating member in contact with the assembly surface of the head part.

An alignment guide which has at least one pivoting arm can be used with head parts which have different sizes.

Optionally, the axial portion includes first and second arms which are connected to the axial portion at its widest point so that they can be pivoted relative to the axial portion between a retracted position which allows a head part to be located within the said space and a deployed position in which a head part position in the said space is retained therein.

When the alignment guide includes first and second pivotably mounted arms, a shaft which translates relative to the axial portion of the alignment guide can have a camming surface which engages respective camming surfaces on internal surfaces of the arms, causing the arms to be pivotably displaced outwardly when the shaft is translated in a distal direction. The camming surface on the shaft can be provided by the surface of a portion of the shaft which is flared outwardly. This can act on an appropriately located portion of the internal surface of each of the arms. For example, the camming surface in each of the arms can be provided by an inwardly protruding tab on the internal surfaces of the arms. The outward displacement of the camming surfaces can disengage the distal portion of each arm from the assembly surface of the head part as the head part and the stem or other part of the prosthesis component are assembled.

An alignment guide which has two or more pivoting arms can be engaged with a head part and then used to move or otherwise manipulate the head part. This can be particularly useful when the head part is being manipulated during preparatory steps prior to a surgical procedure. For example, the alignment guide can be engaged with a head part which is presented in its packaging, and then used to remove the head part from the packaging. The alignment guide can be used to position the head part on a spigot on a stem part. These steps can be performed without any need to touch the head part. This can help to preserve a polished finish on the bearing surface of the head part.

The at least one arm should have sufficient rigidity to ensure that it is not deformed unacceptably when in use.

The at least one arm can have openings which allow the head part to be inspected when it is mounted within the alignment guide. The openings also reduce the weight of the alignment guide.

The distal portion of the arm or arms functions as an assembly surface seating member. Hereinafter the distal portion of the arm is interchangeably referred to as an "assembly surface seating member".

Optionally, the assembly surface seating member can be provided by an in-turned lip at or near the end of the arm.

The assembly surface seating member can include one or more surface features which engage positively with the assembly surface of a head part. This can ensure that the head part and the assembly surface seating member can be assembled with a single stable position relative to one another. The head part can be held within the alignment guide as a result of engagement of the surface features with the assembly surface against transverse movement. The bore in the assembly surface of the head part is aligned with the second axis defined by the axial portion when the surface features on the assembly surface are engaged positively with the assembly surface of a head part. This ensures that the second axis (as defined by the axial portion) along which force is applied to the head part of the prosthesis component is aligned with the first axis (as defined by the bore). An example of a surface feature is a recess which can engage the head part around at least part of the external periphery of the assembly surface. The recess can be continuous. The recess could be defined by one or more protrusions which engage the assembly surface of the head part at spaced apart points around the head part. A surface feature could include one or more protrusions which fit into corresponding detents formed in the assembly surface.

The assembly surface seating member can be shaped so that it restricts transverse movement of the head part of the prosthesis component. For example, the assembly surface seating member can engage an edge of the assembly surface of the head part. The edge of the assembly surface can be an outside edge. The outside edge of the assembly surface might be at or close to an outside edge of the head part when the head part is shallow (for example when the depth of the head part is less than half of its width, as can be the case with the humeral component of a shoulder prosthesis). The outside edge of the assembly surface might be at the interface between the rounded bearing surface of the head part and the assembly surface. The assembly surface might have a chamfer portion which is located between the rounded bearing surface and the bore. The outside edge of the assembly surface might be at the interface between the rounded bearing surface of the head part and the chamfer portion of the assembly surface. The lip might engage other features on the assembly surface. For example, the assembly might make use of one or more protrusions on one of the assembly surface seating member and the assembly surface of the head part and one or more detents on the other of the assembly surface seating member and the assembly surface.

The assembly surface seating member can include a series of surface features which can engage with the assembly surfaces of a plurality of distinct head parts having different sizes. For example, an assembly surface seating member can be provided with a series of recesses, each of which is configured to engage a respective head part. For example, when the assembly surfaces on the head parts are circular in outline, the recesses can be concentric, with each one shaped as part or the whole of a circle. The head part can be restrained against translation relative to the assembly surface seating member when it is engaged with its respective recess.

It is also envisaged that the surface of the assembly surface seating member might be free of interruptions so that the assembly surface of a head part can translate across the surface of the assembly surface seating member. The surface could be essentially planar. The surface might be profiled so as to promote centring of the head part. For example, it might be concave with a centre which is aligned with the centre of the bore in a head part when properly positioned on the surface. The head part can be located appropriately on the assembly surface seating member as a result of engagement between the bearing surface seating member and the bearing surface, causing the assembly surface to translate on the surface of the assembly surface seating member until it is properly centered. An alignment guide having these features might accommodate a plurality head parts having different sizes. For example, head parts with different sizes, and therefore with differently sized assembly surfaces, can contact different regions of the second seating member. The different regions can be arranged concentrically when the head parts are circular.

It can be preferred that the assembly surface seating member engages the assembly surface of the head part at least three spaced apart points. The assembly surface seating member can be provided in multiple sections on respective arms which extend separately from the axial portion, with each section of the assembly surface seating member engaging the assembly surface at a respective point around the assembly surface. For example, when the alignment guide provides an in-turned lip at the distal end of a narrow arm, it can be preferred that there are at least three such arms whose in-turned lips can engage the assembly surface of the head part at three spaced apart points around the assembly surface. Sections of the assembly surface seating member can be provided on two arms where each section is approximately U-shaped. The two arms can be positioned next to one another so that the sections of the assembly surface seating member together extend almost around the entire assembly surface of the head part apart possibly from small breaks at the gaps between the arms. The assembly surface seating member can have a slot formed in it which is open to one side so that it is approximately U-shaped. These arrangements can help to ensure that the head part of the prosthesis component is located positively relative to the alignment guide.

In some constructions, the alignment guide can include a deployable retainer which, when deployed, can help to retain the head part within the space between the bearing surface seating member and the assembly surface seating member. The retainer can be deployed to close at least partially the opening through which the head part is inserted into the space between the seating members. The retainer can slide between deployed and retracted positions. When the space between the seating members is shaped to receive a generally spherical head part, the retainer can be shaped so as to follow a generally spherical contour. A retainer which can follow a generally spherical contour can be retracted to a position in which it is in a surface-to-surface facing relationship with an adjacent wall portion of the alignment guide.

An alignment guide can include a deployable retainer in addition to a bearing surface seating member which is formed from a resiliently deformable material and engages the head part of the prosthesis component with a press fit.

In some constructions, the alignment guide can have stand surfaces which enable it to be positioned on a surface while a head part is positioned within the alignment guide. For example, when an alignment guide has two or more pivoting arms with which it can be engaged with a head part and then used to move or otherwise manipulate the head part, each of the arms can have stand surfaces which enable the guide to be positioned on a flat surface with each of the stand surfaces in contact with the surface. This can be convenient during preparatory steps prior to a surgical procedure, minimizing the need for a user to contact surfaces of the head part directly, and avoiding the need for the head part itself to be placed in contact with the flat surface.

It will often be preferred that some or all of the components of the alignment guide are made from a polymeric material. This has the advantage of light weight compared with components made from metals. Components made from polymeric materials can be manufactured conveniently using moulding techniques. Components made from certain polymeric materials can be less likely to damage (for example by scratching) a polished surface such as a prosthesis component bearing surface compared with components made from a metal.

The invention also provides a method of assembling an orthopaedic joint prosthesis, which comprises:

a. providing an assembly according to the invention together with another part of the orthopaedic joint prosthesis component which has a spigot which can be received in the bore in the head part, b. mounting the head part of the orthopaedic joint prosthesis component within the alignment guide so that the distal portion of the arm is engaged with the assembly surface of the head part, and the axial portion engages, either directly or indirectly, the bearing surface of the head part, c. locating the spigot on the other part of the prosthesis component in the bore in the head part, and d. applying an impaction force to the head part through the axial portion, in which the impaction force applied to the second axis as defined by the axial portion is directed along the first axis as defined by the bore in the head part.

The invention also provides a method of implanting an orthopaedic joint prosthesis, which comprises:

a. providing an assembly according to the invention together with another part of the orthopaedic joint prosthesis component which has a spigot which can be received in the bore in the head part, b. mounting the head part of the orthopaedic joint prosthesis component within the alignment guide so that the distal portion of the arm is engaged with the assembly surface of the head part, and the axial portion engages, either directly or indirectly, the bearing surface of the head part, c. locating the spigot on the other part of the prosthesis component in the bore in the head part, and d. applying an impaction force to the head part through the axial portion, in which the impaction force applied to the second axis as defined by the axial portion is directed along the first axis as defined by the bore in the head part.

In which the said other part of the orthopaedic joint prosthesis component is implanted in a patient's bone prior to the step of applying an impaction force.

The invention is described below by way of example with reference to the accompanying drawings, in which:

FIG. 7 is an isometric view from above of an alignment guide and the head part of a femoral component of a hip joint prosthesis.

FIG. 8 is an isometric view from below of the alignment guide and head part shown in FIG. 7.

FIG. 9 is an isometric view of an orthopaedic joint prosthesis assembly comprising a modular femoral component of a hip joint prosthesis and the alignment guide shown in FIG. 7.

Figure 1:
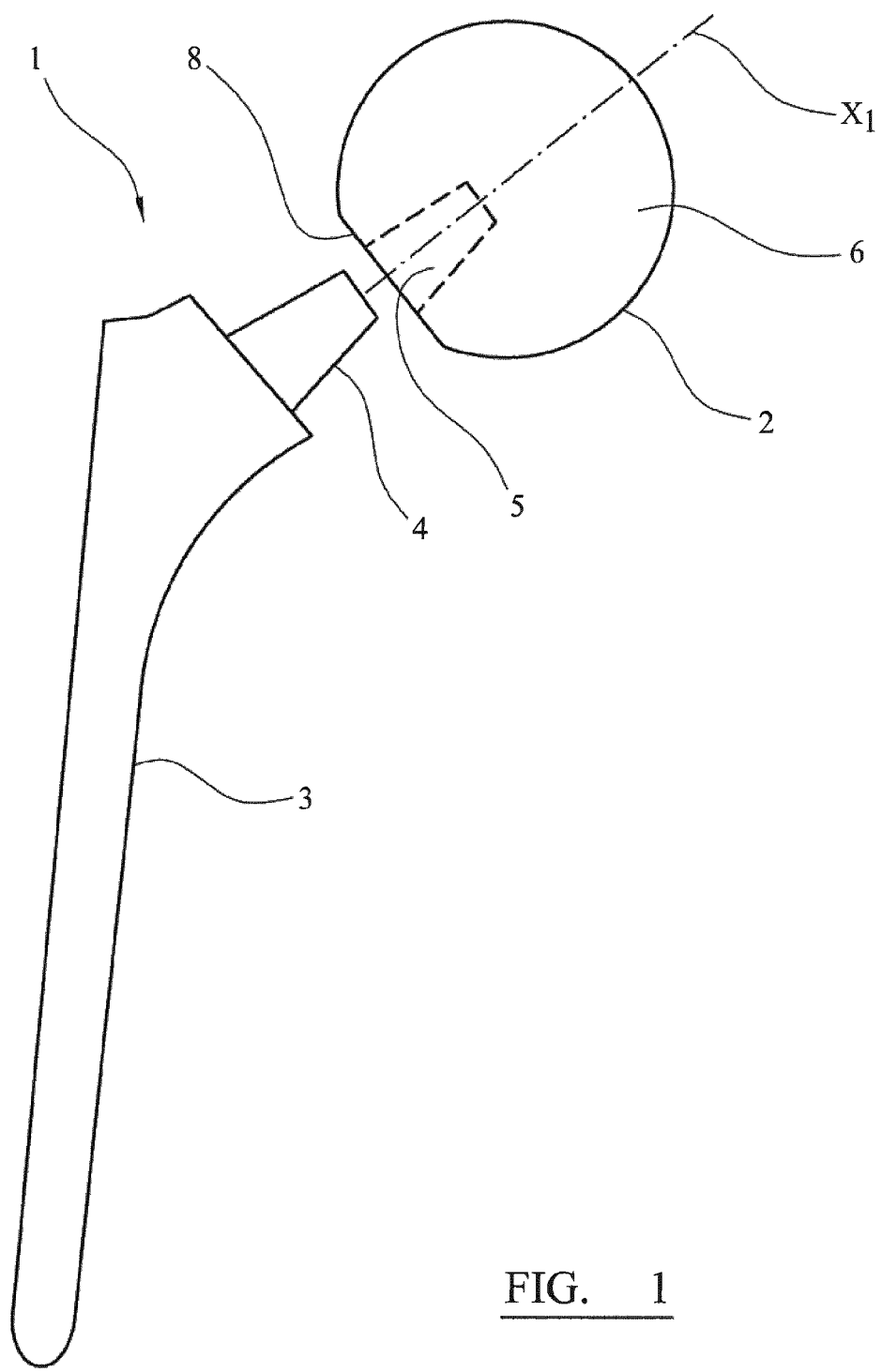
FIG. 1 is a side view of a modular femoral component of a hip joint prosthesis.

Referring to the drawings, FIG. 1 shows a femoral component 1 of a hip joint prosthesis which includes a head part 2 and a stem part 3. The stem part 3 is configured to be implanted in the intramedullary cavity of a patient's femur.

The head part 2 has a smooth outer bearing surface 6 which is intended to articulate with a corresponding joint surface. The corresponding joint surface will usually be provided by an acetabular component of the hip joint prosthesis. However, it might be that a head part might be intended to articulate with a corresponding joint surface provided by the patient's natural tissue. The outer bearing surface has a generally spherical shape, which is truncated to define an assembly surface 8. A tapered bore 5 is formed in the head part, extending inwardly from the assembly surface, perpendicular to the assembly surface. The first axis 7 of the head part extends perpendicular to the assembly surface and is defined by tapered bore 5.

The assembly surface is at one end of the axis 7 and the centre of the bearing surface is at the opposite end of the axis. The assembly surface surrounds the bore. The assembly surface is generally planar, defined by a straight line when the head part is viewed in cross-section. The flat portion extends annularly around the opening to the bore in the head part. The flat portion is planar, containing the plane of the opening to the bore in the head part.

The stem part 3 includes a tapered spigot 4. The tapered spigot on the stem part and the tapered bore in the head part are configured so that they can form a self-locking taper lock when the head and stem parts are assembled. Preferably, the angle between the tapered surface of each of the spigot and the bore and the longitudinal axis of the spigot and the bore (when the part is viewed in cross-section) is about 1.4° to about 1.5°.

Figure 2:
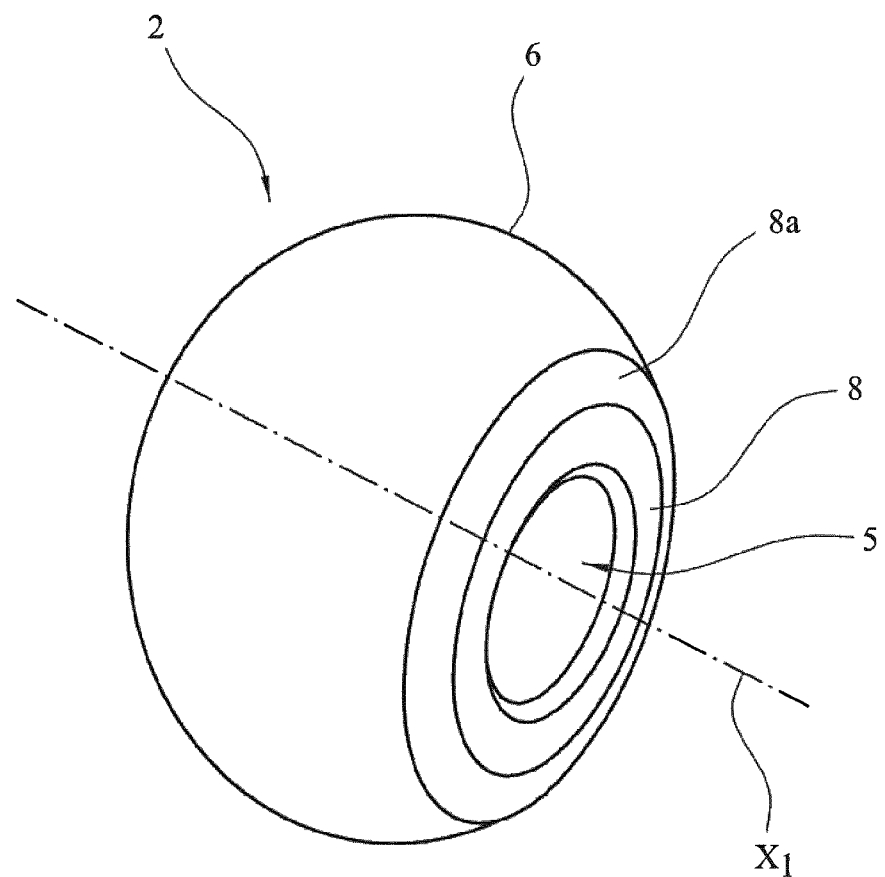
FIG. 2 is an isometric view of a head part of a femoral component of a hip joint prosthesis.

FIG. 2 shows another head part of a femoral component of a hip joint prosthesis. The assembly surface includes a planar portion 8 surrounding the bore 5, which lies in a plane which is perpendicular to the axis defined by the bore. The assembly surface also includes an annular chamfer portion 8a which is located between the planar portion 8 and the bearing surface 6 of the head part. The chamfer portion extends around the head part, and which is inclined to the plane which is defined by the opening to the bore in the head part when the head part is viewed in cross-section. The assembly surface could include an annular portion which is curved, generally in a convex sense, when the head part is viewed in cross-section. When the assembly surface has a chamfer portion or a curved portion without a planar portion, there will be a narrow ridge surrounding the opening to the bore 5.

Figure 3:
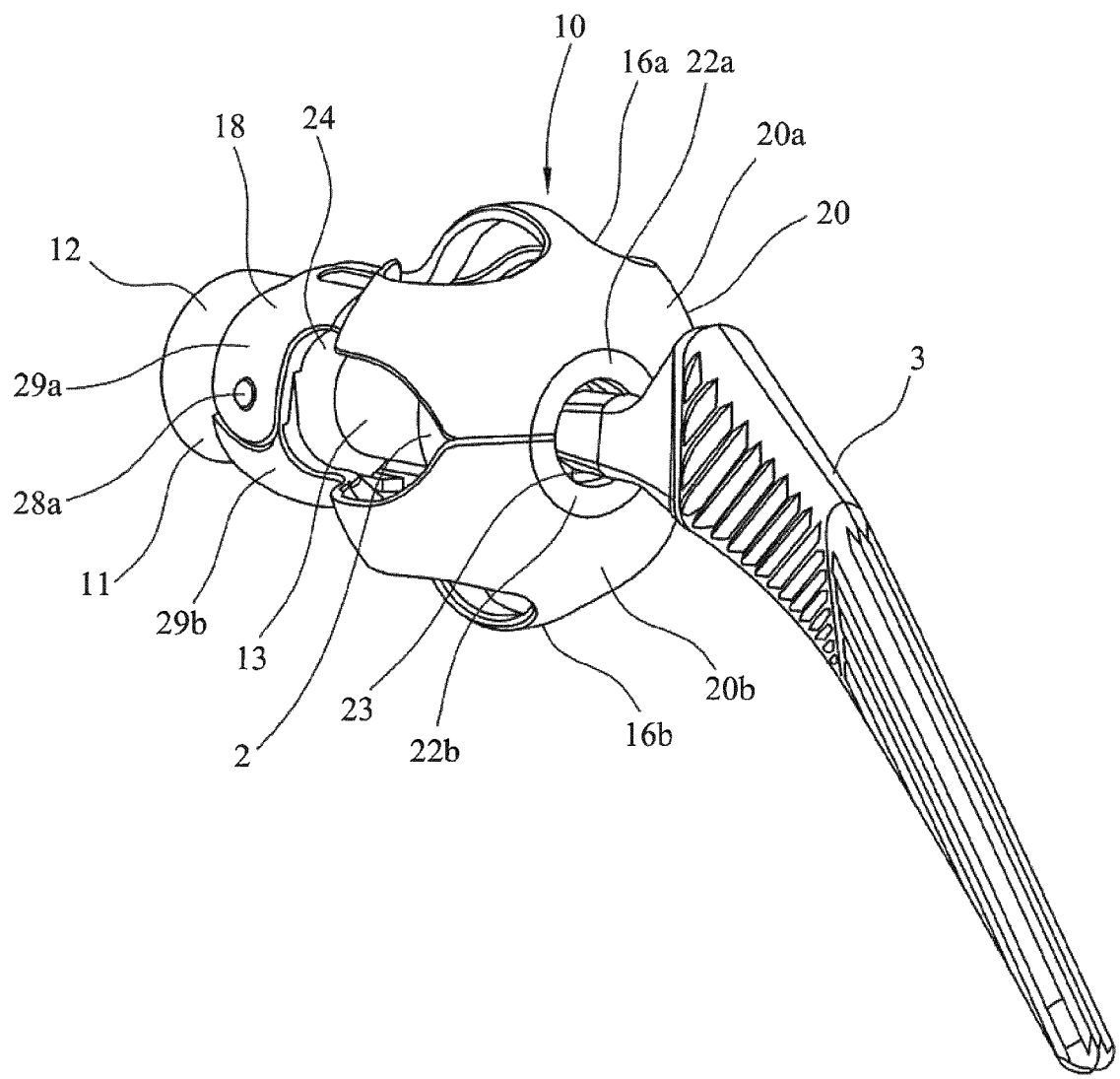
FIG. 3 is an isometric view of an orthopaedic joint prosthesis assembly comprising a modular femoral component of a hip joint prosthesis and an alignment guide for use in assembling the femoral component.

FIG. 3 shows an orthopaedic joint prosthesis assembly which includes the femoral component 1 shown in FIG. 1 and an alignment guide 10 for use in assembling the stem and head parts 2, 3 of the femoral component.

Figure 5:
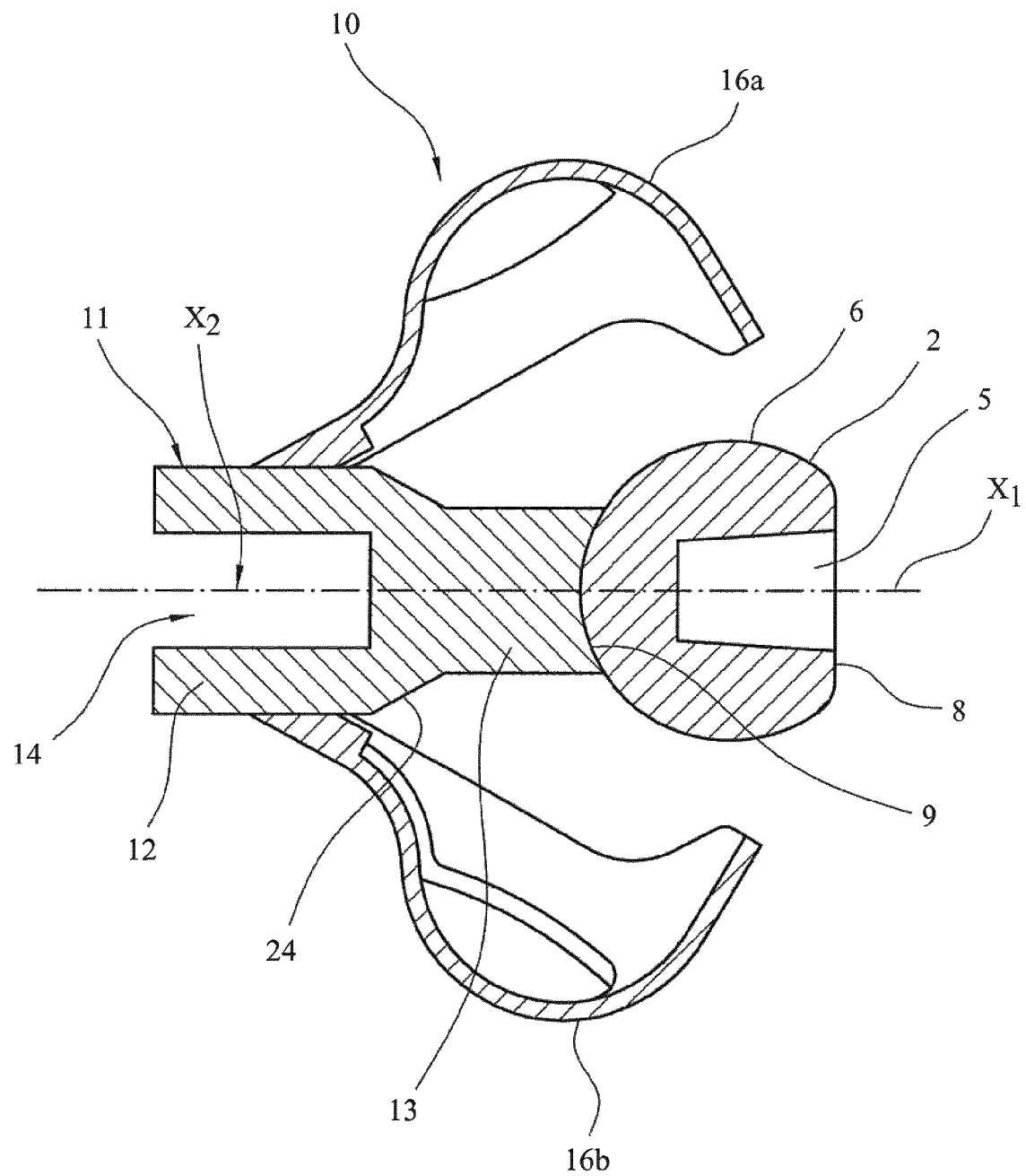
FIG. 5 is a cross-section of the alignment guide shown in FIG. 3 with the arms in an open position.
Figure 6:
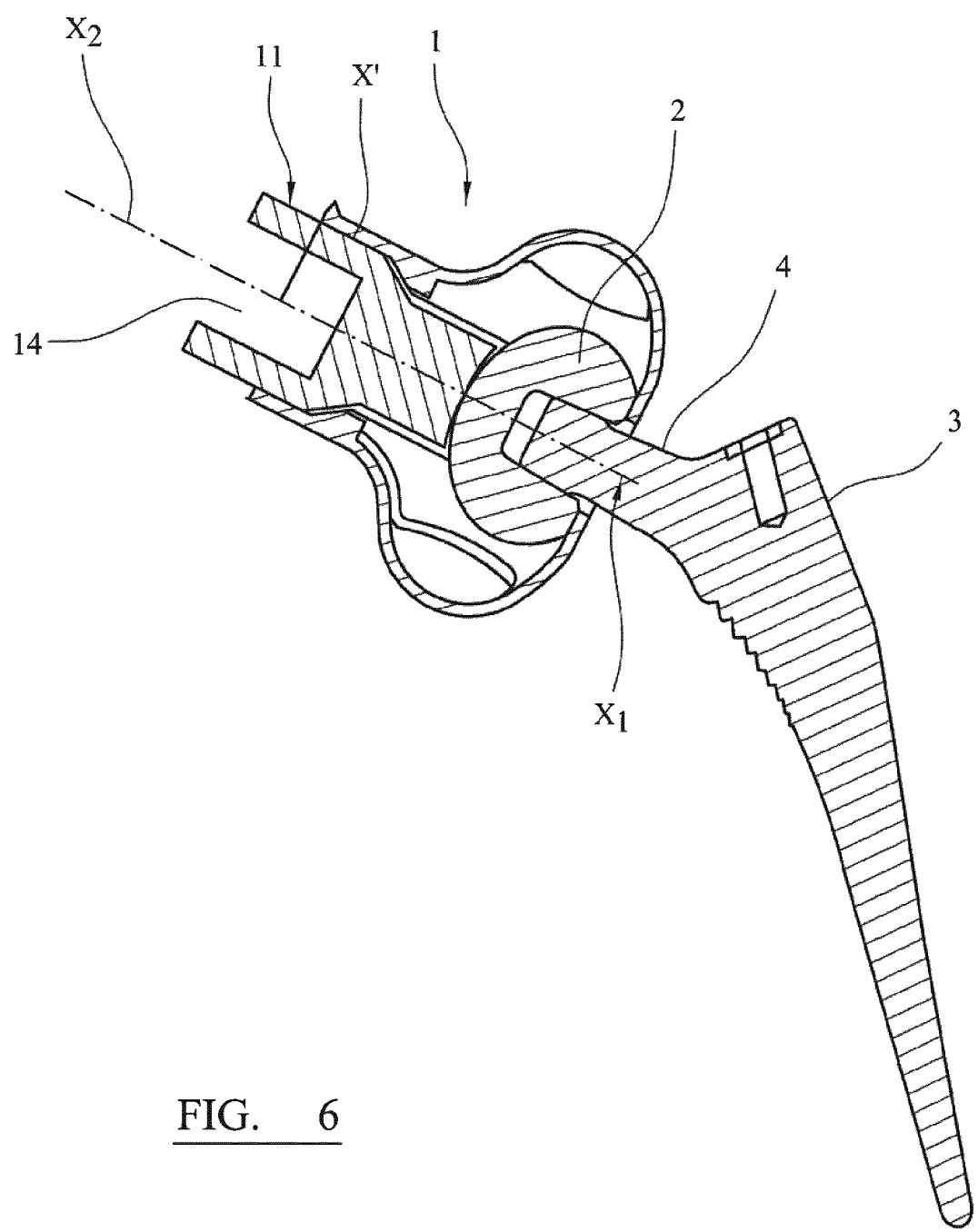
FIG. 6 is a cross-section of the alignment guide shown in FIG. 3 together with the femoral component.

The alignment guide 10 comprises an axial portion in the form of a shaft 11 and arms 16a, 16b extending therefrom. The shaft has first and second portions 12, 13 and carries an impaction tip 15 which can contact the bearing surface of a head part of a femoral prosthesis component, functioning as a bearing surface seating member. The shaft defines a second axis $X_2$ (as shown in FIG. 5). The diameter of the first portion 12 of the shaft is greater than that of the second portion 13. A tapered portion 24 of the shaft extends between the first and second portions. In the construction shown in the drawings, the shaft 11 has a bore 14 in the first portion 12 at its free end in which the end of an impaction device can be received through which an impaction force can be applied to the impaction component. However, the shaft might be acted on directly by an impaction device such as a mallet. The surface of the impaction tip 15 is concave, to match the convex bearing surface of the head part 2 of the femoral component.

Each arm 16a, 16b includes a collar portions 18a, 18, a neck portion 19a, 19b and a head portion 20a, 20b. Each collar portion 18a, 18b comprises a pair of curved projections 29a, 29a'; 29b, 29b' which have a partially cylindrical profile and are dimensioned to fit around a portion of the exterior surface of the first portion 12 of the shaft 11. The two arms 16a, 16b are pivotally connected to one another at the collar portions 18a, 18b. The pivotal connections are achieved by providing a lug 28a, 28b on one of the curved projections 29a', 29b of the collar portions 18a, 18b of the arms 16a, 16a, and an aperture 30a, 30b on the other curved projection 29a, 29b' of the respective collar portions 18a, 18b of the arms 16a, 16a. A lug 28a, 28b cooperates with a respective aperture 30a, 30b to define a pivot point 31a, 31b.

Figure 4:
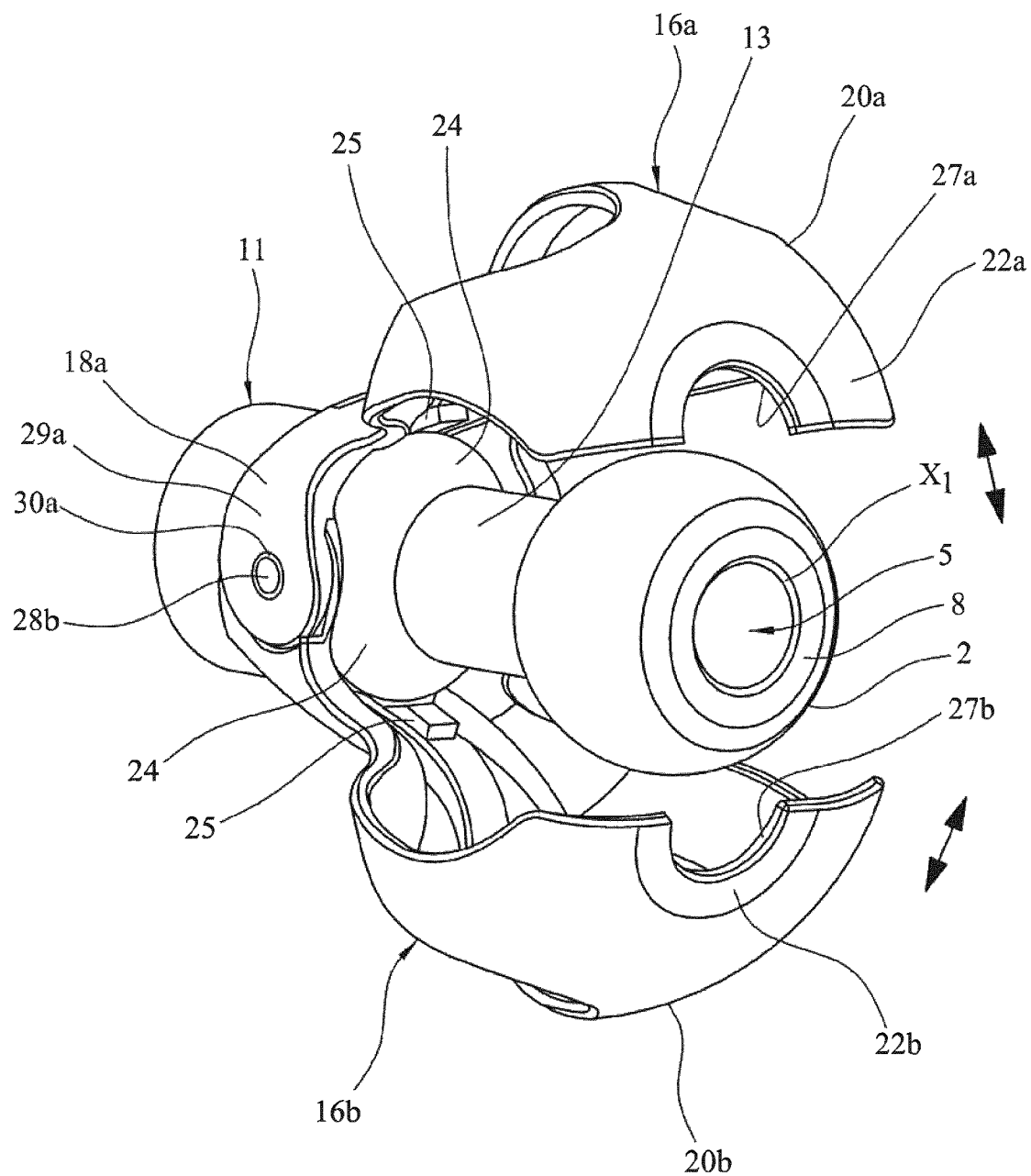
FIG. 4 is an isometric view of the alignment guide shown in FIG. 3 and the head part of the femoral component, with the arms of the alignment device in an open position.

The arms 16a, 16b are substantially the same and have a curved, bowl-shaped, contour such that when they abut each other in a closed position, the two arms 16a, 16b define an internal cavity or space 17 which encloses the femoral head part 2. This is shown in FIG. 4.

The arms 16a, 16b are shaped so that the neck 19 is circular in cross-section and defines a hollow cylinder with a diameter substantially similar to that of the collar 18.

The distal portion of each of the arms 16a, 16b, i.e., the portion of each arm remote from the collar portions 18a, 18, has an in-turned lip 22a, 22b. When the arms are in their closed position, the lips 22a, 22b form an almost continuous annular surface which faces towards the collar 18, with just small discontinuities at the interfaces between the arms. An opening 23 is provided in the end of the alignment guide by semi-circular cut-outs 27a, 27b in the ends of the arms 16a, 16b. The opening 23 is larger than the opening of the bore 5 into the assembly surface 8 of the head part 2 so that access to the recess 5 is not obscured by the lips 22a, 22b.

The arms 16a, 16b include windows 32 in the side walls of the head portions 20a, 20b which reduce the weight of the alignment guide 10. The windows also allow a user to inspect the femoral head part within the internal cavity 17.

Each of the neck portions 19a, 19b includes a tab 25 with an inclined surface 26 which engages and cooperates with the inclined surface 24 of the impaction component 11 when the alignment guide 21 is in a first, unactuated position. The tabs 25 are provided internally of the neck 19 of the alignment guide 21.

In use, the spigot 4 on the stem part 3 of the femoral component is located in the bore 5 in the head part 2 and the head and stem parts are pressed together.

The head part is then located in the space 17 while the arms 16a, 16b are in their open position, so that the bearing surface 6 is in contact with the impaction tip 15. The arms are then pivoted to their closed position in which the lips 22a, 22b engage the assembly surface 8 on the head part 2 so that the head part is located between the impaction tip 15 and the lips 22a, 22b. The spigot 4 on the stem part then extends through the opening 23 provided by the semi-circular cut-outs 27a, 27b in the ends of the arms. The engagement of the annular surface provided by the lips 22a, 22b with the assembly surface determines the orientation of the head part relative to the alignment guide, in particular so that the first axis $X_1$ defined by the bore 5 in the head part 2 is coincident with the second axis $X_2$ which is defined by the shaft 11 of the alignment guide 10. This ensures that when an impaction force is applied along the second axis $X_2$ the force is directed along the first axis $X_1$.

An impaction force is applied to the shaft 11 through an impaction rod which is inserted into the bore 14 in the end of the first portion 12 of the shaft. Alternatively, the impaction force could be applied direction to the shaft. The impaction force is transmitted through the shaft to the head part of the femoral component, which involves translation of the shaft relative to the alignment guide 21. The translation of the shaft, with the tapered portion 24 of the shaft in contact with the tabs 25 on the internal surfaces of the neck 19 of the alignment guide 21, causes the arms 16a, 16b to pivot outwardly, reducing the contact between the lips 22a, 22b and the assembly surface 8 of the head part.

FIGS. 7 to 9 show an orthopaedic joint prosthesis assembly which includes a head part 100 of a femoral component such as that shown in FIG. 2 and an alignment guide 110 for use in assembling the stem and head parts of a femoral component. The head part 100 of the femoral component can be fitted to a stem part having a tapered spigot at its proximal end. The head part 100 has a bearing surface 104 and a bore 106 in an assembly surface 108. The bore defines a first axis $X_1$. The assembly surface can include a flat planar portion which lies in the plane defined by the opening to the bore in the head part, and a chamfer portion 108a between the flat planar portion and the bearing surface of the head part. The chamfer portion extends around the head part which is inclined to the plane which is defined by the opening to the bore in the head part when the head part is viewed from one side in cross-section.

The alignment guide 110 comprises an axial portion in the form of a hub spar 112, First and second arms 114, 116 extend from the hub spar. The hub spar is curved with a concave inner surface 118 which defines a space within it. The hub spar has a socket 132 formed in it in. The centre of the socket 132 defines a second axis X2. A sleeve component 134 can be provided in the socket as shown in FIG. 9. A shall 142 can extend through the sleeve component and is a sliding lit therein. When the tool includes a sleeve component, the first and second arms can have semi-circular cut-outs so that the arms can fit snugly against the sleeve component.

Each of the arms 114, 116 is connected to the hub spar at the first and second pivot points 122, 124 so that each of the arms can pivot relative to the spar. Each of the arms has a tab 126 which can be engaged by a user to move the arm between its deployed position as shown in the drawings and a retracted position in which each of the arms is pivoted towards the hub spar.

The hub spar includes first and second extensions 128, 130 beyond the pivot points 122, 124. Each of the extensions has a flat surface 134 at its end.

Each of the arms 114, 116 has a lug 136 mounted on its tab 122. The lugs have inner surfaces 138 and outer surfaces 140. The inner surfaces of the lugs are directed towards one another when the arms are in their deployed positions (which is the case as shown in the drawings).

The space which is defined by the inner surface 118 of the hub spar 112 is sized to receive the head part 100. When the bearing surface 104 of head part is shaped as part of a sphere, the concave inner surface of the hub spar will also be shaped as part of a sphere. The pivot points 122, 124 can be provided on the hub spar at its widest point. The width of the space which is defined by the hub spar is greatest between the pivot points. The width of the space which is defined between the extensions 128, 130 is less than that between the pivot points.

The hub spar 112 and the arms 114, 116 can be formed from a polymeric material, for example by injection moulding. Examples of a suitable polymeric material include certain polyamides, polyesters, polyolefins and poly(phenyl sulphones). A suitable material should be capable of withstanding conditions to which it is exposed during manufacture (including sterilization) and use. A suitable material will often be resiliently deformable.

In use, the head part 100 of a femoral prosthesis component can be fitted into the alignment guide 110 when the arms 114, 116 are in their retracted positions. This involves displacing the extensions 128, 130 at the ends of hub spar 112 outwardly so that the widest part of the spherical bearing surface 104 is positioned beyond the extensions 128, 130, generally in line with the pivot points 122, 124. The resilient deformability of the material of the hub spar means that the head part is retained within the space 120 defined by the hub spar by means of the extensions.

Once the head part has been positioned within the space defined by the hub spar, the arms 114, 116 are pivoted from their retracted positions to their deployed positions. This can be performed by a user by engaging the tabs 122, for example with the finger and thumb of one hand. The inner surfaces 138 of the lugs 136 engage the chamfer surface portion 108a of the head part at diametrically opposite points of the chamfer surface. The head part is then located between the concave surface of the hub spar which contacts the bearing surface and the lugs 136 which contact the assembly surface, the concave surface of the hub spar and the lugs being the bearing surface seating member and assembly surface seating members respectively.

The outer surfaces 140 of the lugs 136 and the flat surfaces 134 at the ends of the extensions are approximately coplanar. The assembly of the head part 100 and the alignment guide 110 can be placed on a surface (for example a table) with the outer surfaces 140 of the lugs 136 and the flat surfaces 134 at the ends of the extensions in contact with the table. The head part 100, including in particular the assembly surface 108a of the head part, is visible for inspection between the lugs and the extensions. The head part 100 can be manipulated by a user gripping the alignment guide, including positioning the head part so that the spigot on the stem part of the femoral component is received within the bore 106 in the head part. It is not necessary to contact the bearing surface of the head part.

The engagement between the hub spar 112 and the lugs 136 against the head part ensures that the head part is located centrally within the alignment guide with the first axis $X_1$ that is defined by the bore in the head part being coincident with the second axis $X_2$ defined by the centre of the socket 132 in the hub spar.

An impaction force can be applied to the head part to achieve a secure connection between it and the stem part through an impaction shaft 142 which extends through the bore in the sleeve component 134. The sleeve component ensures that the longitudinal axis of the shaft extends perpendicular to the plane of the socket 132 in the hub spar, and is coincident with the second axis $X_2$ defined by the centre of the socket. An impaction force that is directed through the impaction shaft 142 is therefore coincident with the first axis $X_1$ that is defined by the bore in the head part. This ensures that when an impaction force is applied along the second axis $X_2$ the force is directed along the first axis $X_1$.

Figure 10:
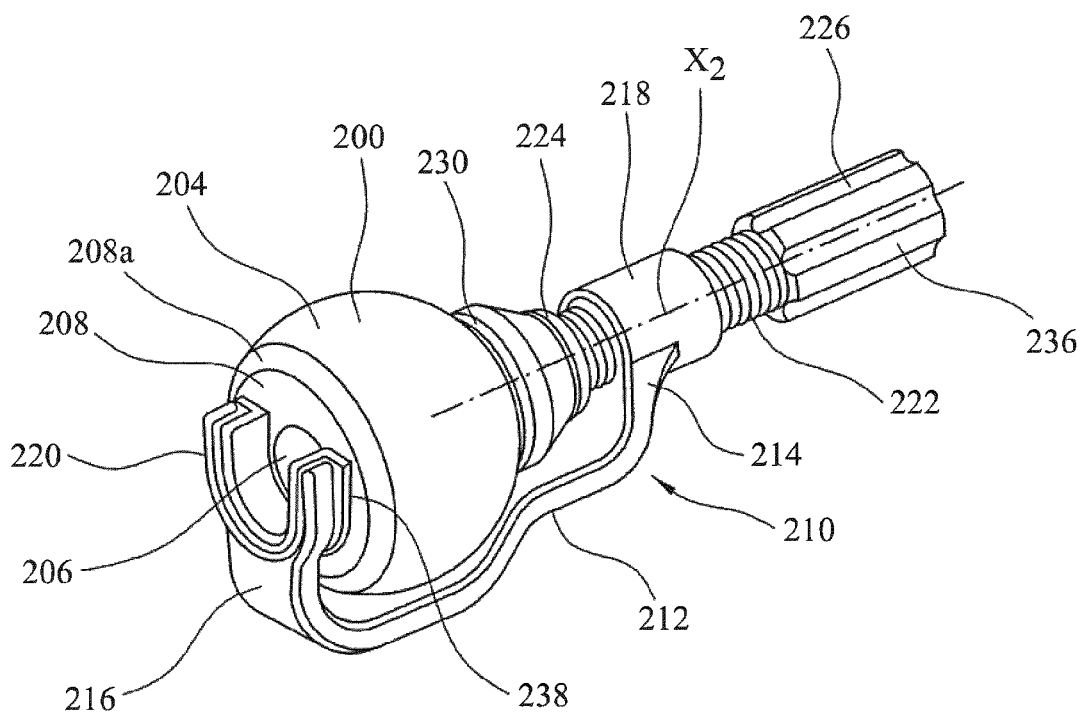
FIG. 10 is an isometric view of another orthopaedic joint prosthesis assembly comprising a modular femoral component of a hip joint prosthesis and the alignment guide.
Figure 11:
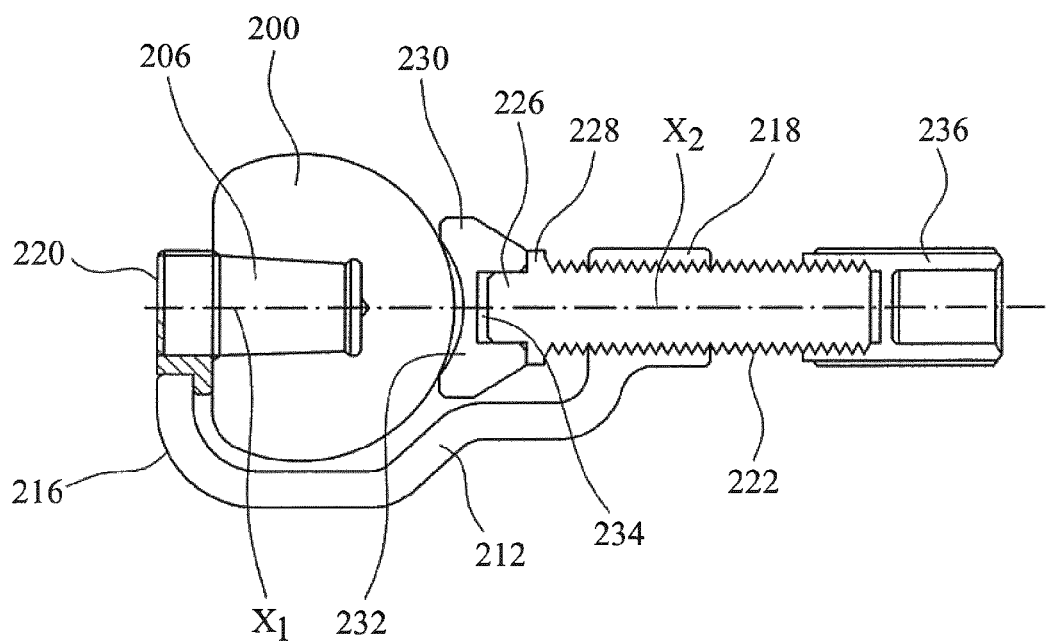
FIG. 11 is a cross-section through the assembly shown in FIG. 10.

FIGS. 10 and 11 show an orthopaedic joint prosthesis assembly which includes a head part 200 of a femoral component such as that shown in FIG. 2 and an alignment guide 210 for use in assembling the stem and head parts of a femoral component. The head part 200 of the femoral component can be fitted to a stem part having a tapered spigot at its proximal end. The head part 200 has a bearing surface 204 and a bore 206 in an assembly surface 208. The assembly surface includes a chamfer portion 208a.

The alignment guide 210 comprises an axial portion in the form of a threaded sleeve 218. The threaded sleeve defines a second axis $X_2$ which, when the head part of an orthopaedic joint prosthesis component is mounted within the alignment guide, is coincident with the first axis $X_1$ defined by the bore 206. An arm 212 having proximal and distal ends 214, 216 extends in a distal direction from the threaded sleeve 218. The distal end 216 of the arm 212 has a U-shaped bracket 220.

A threaded shaft 222 extends through the sleeve. The longitudinal axis of the shaft 222 is coincident with the longitudinal axis of the sleeve 218. The thread on the shaft 222 engages the thread in the sleeve 218 so that the shaft can be advanced and retracted through the sleeve by rotating the shaft relative to the sleeve. The shaft has a first end 224 which is closer to the second end 216 of the arm 212, and an opposite second end 226.

The shaft 222 has a boss 226 at the end of the shaft which is closer to the second end 216 of the arm 212. The boss is defined by a shoulder 228 on the shaft.

The alignment guide includes a circular seating member 230 which has a concave surface 232 defined by a part of a sphere on one side. It has a recess 234 on its opposite side which can receive the boss 226 on the end of the shaft. The curvature of the concave surface of the circular seating member corresponds approximately to the curvature of the bearing surface 204 of the head part 200 so that the head part fits against the seating member. The engagement between the recess on the seating member and the boss on the end of the shaft means that the seating member can remain stationary in contact with the bearing surface of the head part when the shaft is rotated.

The shaft 222 carries a socket member 236 at the second end 226 of the shaft. The socket member can receive the end of an impaction rod through which an impaction force can be applied. An impaction force can be applied using a mallet or using an instrument such as the one disclosed in EP-A-1707160. The external surface of the socket member 236 is ridged to facilitate gripping the socket member to twist it and the shaft.

The U-shaped bracket 220 carries a U-shaped seating member 238 which is also U-shaped. The space between the arms of the seating member is at least equal to the diameter of the bore 206 in the head part 200. It will usually be slightly bigger than the diameter of the bore. The seating member is made from a polymeric material such as a poly(phenyl sulphone). The surface of the seating member which faces the proximal end of the arm is smooth.

In use, the head part 200 of a femoral prosthesis component can be fitted into the alignment guide 210 when the threaded shaft 222 is retracted so as to create sufficient space between the circular seating member 230 on the end of the shaft and the U-shaped seating member 238 at the second end of the arm 212, so that the head part is positioned in the space between the two seating members 230, 238. The shaft is retracted in this way by rotating it relative to the sleeve 218.

The threaded shaft 222 is then advanced through the sleeve 218 by rotating it relative to the shaft to drive the concave surface 232 of the circular seating member into contact with the bearing surface 204 of the head part 200. This leads to surface to surface contact between the assembly surface 208 of the head part and the exposed face of the U-shaped seating member 238. The head part becomes centered on the U-shaped seating member as the circular seating member becomes seated on the bearing surface of the head part by translating across the U-seating member due to the action of the circular seating member against the bearing surface. The first axis $X_1$ which is defined by the bore 206 in the head part then extends through the centre of the circular seating member 230 and is coincident with the second axis $X_2$ which is defined by the sleeve 218.

An impaction force can be applied to the head part to achieve a secure connection between it and the stem part through the shaft 222. An impaction force that is directed through the impaction shaft, positioned within the sleeve 218, is therefore coincident with the first axis $X_1$ that is defined by the bore 206 in the head part 200. This ensures that when an impaction force is applied to the shaft 222 along the second axis $X_2$ the force is directed along the first axis $X_1$.

Figure 12:
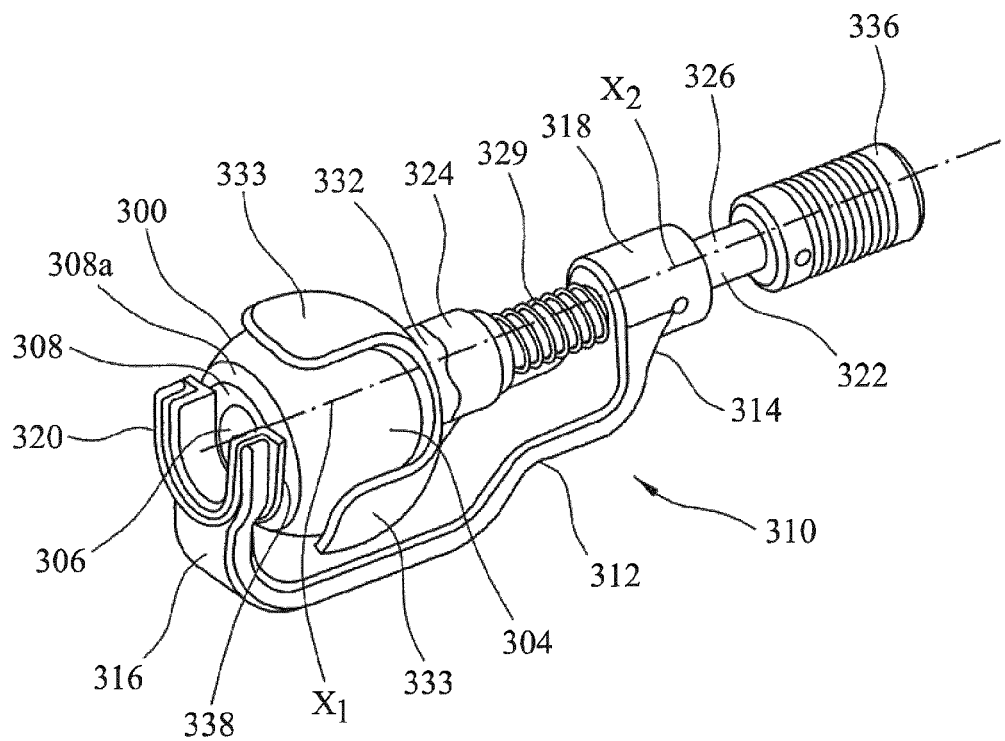
FIG. 12 is an isometric view of another orthopaedic joint prosthesis assembly comprising a modular femoral component of a hip joint prosthesis and the alignment guide.
Figure 13:
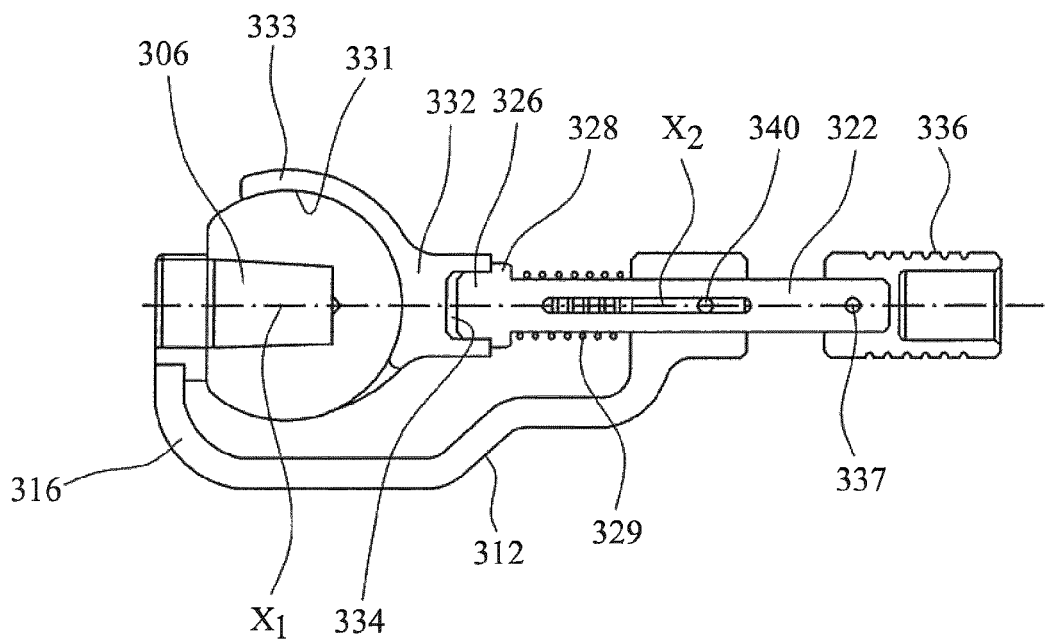
FIG. 13 is a cross-section through the assembly shown in FIG. 12.

FIGS. 12 and 13 show an orthopaedic joint prosthesis assembly which includes a head part 300 of a femoral component such as that shown in FIG. 2 and an alignment guide 310 for use in assembling the stem and head parts of a femoral component. The assembly has features in common with the assembly which is discussed above with reference to FIGS. 10 and 11. The head part 300 of the femoral component can be fitted to a stem part having a tapered spigot at its proximal end. The head part 300 has a bearing surface 304 and a bore 306 in an assembly surface 308. The assembly surface includes a chamfer portion 308a.

The alignment guide 310 includes an axial portion in the form of a plain bore sleeve 318. The plain bore sleeve defines a second axis $X_2$ which, when the head part of an orthopaedic joint prosthesis component is mounted within the alignment guide, is coincident with the first axis $X_1$ defined by the bore 306. An arm 312 having proximal and distal ends 314, 316 extends in a distal direction from the plain bore sleeve 318. The distal end of the arm 314 includes a U-shaped bracket 320.

A shaft 322 extends through the sleeve. The longitudinal axis of the shaft 322 is coincident with the longitudinal axis of the sleeve 318. The shaft 322 can be advanced and retracted through the sleeve. The shaft has a first end 324 which is closer to the distal end 316 of the arm 312, and an opposite second end 326.

The shaft 322 has a boss 326 at the end of the shaft which is closer to the second end 316 of the arm 312. The boss is defined by a shoulder 328 on the shaft. A spring 329 acts between an end of the sleeve 318 and the boss 326.

The alignment guide includes a three fingered seating member which has a concave surface 331 defined by a part of a sphere on one side. The seating member has a central hub 332 and three fingers 333 extending radially from the hub which provide the concave surface 331. The curvature of the concave surface of the circular seating member corresponds approximately to the curvature of the bearing surface 304 of the head part 300 so that the head part fits against the seating member. The seating member has a recess 334 on the side which is opposite to the concave surface which can receive the boss 324 on the end of the shaft. The engagement between the recess on the seating member and the boss on the end of the shaft means that the seating member can remain stationary in contact with the bearing surface of the head part when the shaft is rotated.

The shaft 322 carries a socket member 336 at the second end 326 of the shaft. The socket member can receive the end of rod through which an impaction force can be applied. The socket member 336 is fastened to the end of the shaft by means of a pin 337. An impaction force can be applied using a mallet or using an instrument such as the one disclosed in EP-A-1707160. The socket member has a series of circumferential ridges which facilitate gripping the socket member to apply an axial force to the shaft, against the action of the spring 329.

The U-shaped bracket 320 carries a U-shaped seating member 338 which is also U-shaped. The space between the arms of the seating member is at least equal to the diameter of the bore 306 in the head part 200. It will usually be slightly bigger than the diameter of the bore. The seating member is made from a polymeric material such as a poly(phenyl sulphone). The surface of the seating member which faces the first end of the arm is smooth, allowing the head part to translate on the seating member as describe above.

In use, the head part 300 of a femoral prosthesis component can be fitted into the alignment guide 310 when the shaft 322 is retracted so as to create sufficient space between the circular seating member 330 on the end of the shaft and the U-shaped seating member 338 at the second end of the arm 312, so that the head part is positioned in the space between the two seating members 330, 338. Retraction of the shaft 322 involves pulling it through the sleeve, compressing the spring 329 between the end of the sleeve 318 and the boss 326. The shaft can be retracted in this way by gripping the socket member 336. The extent of movement of the shaft relative to the sleeve is restricted by means of a pin 340 which is located in a bore in the sleeve and extends through a longitudinal slot in the shaft.

The shaft 322 is then released so that it advances through the sleeve 318, acted on by the spring 329, so that the circular seating member contacts the bearing surface 304 of the head part 300. This leads to surface to surface contact between the assembly surface 308 of the head part and the exposed face of the U-shaped seating member 338. The head part becomes centered on the U-shaped seating member as the circular seating member becomes seated on the bearing surface of the head part by translating across the U-seating member due to the action of the circular seating member against the bearing surface. The first axis $X_1$ which is defined by the bore 306 in the head part then extends through the centre of the circular seating member 330 and is coincident with the second axis $X_2$ which is defined by the sleeve 318.

An impaction force can be applied to the head part to achieve a secure connection between it and the stem part through the shaft 322. An impaction force that is directed through the impaction shaft 3222 is therefore coincident with the first axis $X_1$ that is defined by the bore in the head part. This ensures that when an impaction force is applied along the second axis $X_2$ the force is directed along the first axis $X_1$.

Figure 14:
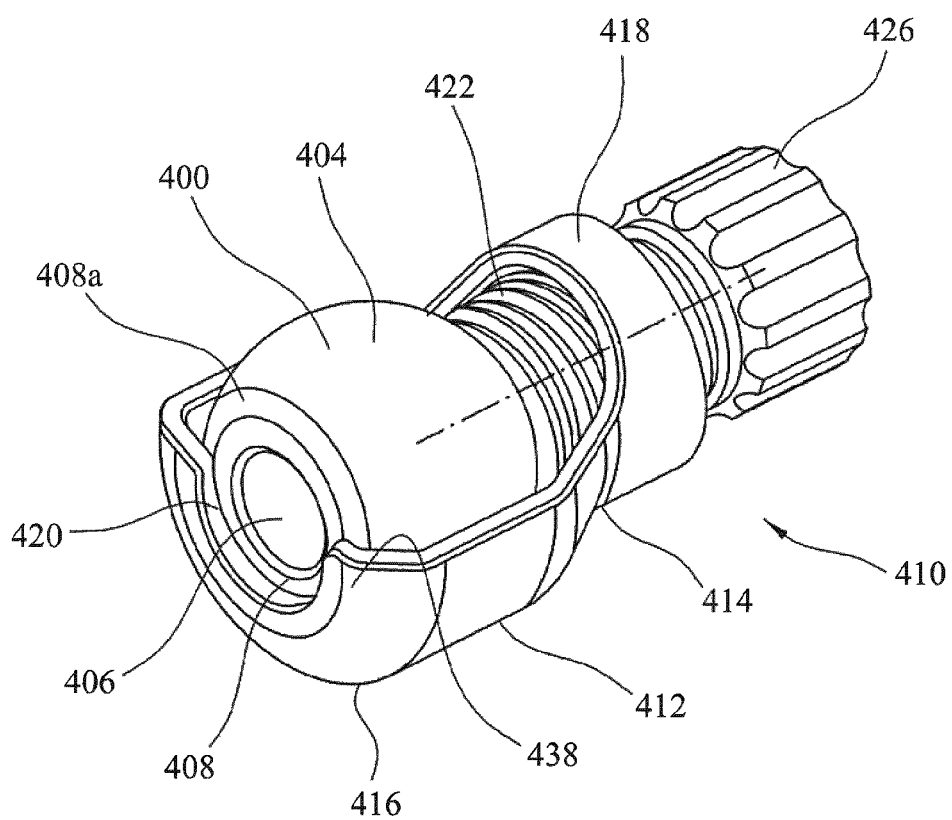
FIG. 14 is an isometric view of another orthopaedic joint prosthesis assembly comprising a modular femoral component of a hip joint prosthesis and the alignment guide.
Figure 15:
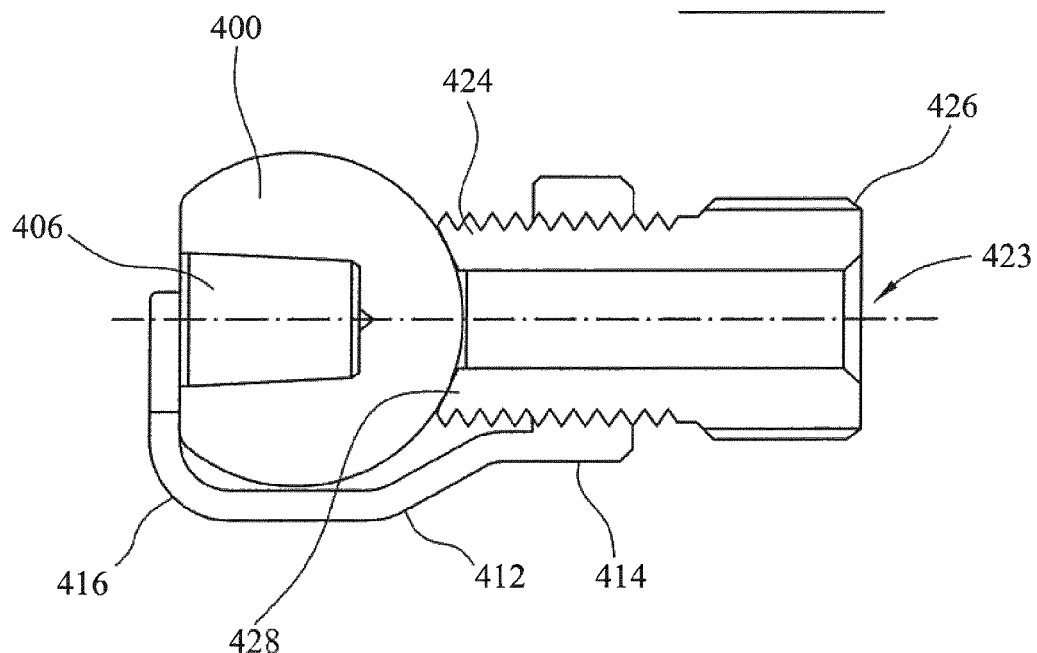
FIG. 15 is a cross-section through the assembly shown in FIG. 14.

FIGS. 14 and 15 show an orthopaedic joint prosthesis assembly which includes a head part 400 of a femoral component such as that shown in FIG. 2 and an alignment guide 410 for use in assembling the stem and head parts of a femoral component. The assembly has features in common with the assembly which is discussed above with reference to FIGS. 10 and 11. The head part 400 of the femoral component can be fitted to a stem part having a tapered spigot at its proximal end. The head part 400 has a bearing surface 404 and a bore 406 in an assembly surface 408. The assembly surface includes a chamfer portion 408a.

The alignment guide 410 includes an axial portion in the form of a threaded sleeve 418. An arm 412 which has proximal and distal ends 414, 416 extends in a distal direction from the sleeve 418. The distal end of the arm has a U-shaped slot 420 in the end wall 438. The arm extends around an angle of arc measured around an axis extending between the proximal and distal ends of about 185 to 190°. It therefore forms a wall which encloses the space between the proximal and distal ends on one side of the alignment guide. The wall can be provided with openings (not shown) to make a head part located within the alignment guide more visible. The arm is made from a polymeric material by moulding. The material is capable of resilient deformation.

A threaded shaft 422 extends through the sleeve. The longitudinal axis of the shaft 422 is coincident with the longitudinal axis of the sleeve 418. The thread on the shaft engages the thread in the sleeve 418 so that the shaft can be advanced and retracted through the sleeve by rotating the shaft relative to the sleeve. The shaft has a first end 424 which is closer to the proximal end 416 of the arm 412, and an opposite second end 426.

The shaft 422 has a 423 bore extending through it which is open at each of the first and second ends 424, 426. The shaft has a ridged collar at the second end which allows the shaft to be gripped in order to rotate it relative to the sleeve 418.

The end wall 428 of the shaft 322 surrounding the open end of the bore 423 is shaped so that it presents a generally concave surface which is an annular portion of a sphere. The end wall is then a circular seating member. The curvature of the concave surface of the circular seating member corresponds approximately to the curvature of the bearing surface 404 of the head part 400 so that the head part fits against the seating member. The engagement between the recess on the seating member and the boss on the end of the shaft means that the seating member can remain stationary in contact with the bearing surface of the head part when the shaft is rotated.

The space between the arms of the U-shaped slot 420 is at least equal to the diameter of the bore 406 in the head part 400. It will usually be slightly bigger than the diameter of the bore.

In use, the head part 400 of a femoral prosthesis component can be fitted into the alignment guide 410 when the threaded shaft 422 is retracted so as to create sufficient space between the circular bearing surface seating member provided by the end 428 of the shaft and the assembly surface seating member provided by the end wall 438 at the distal end of the arm 412. The end wall 438 provides an assembly surface seating member for the head part so that the head part is positioned in the space between the two seating members 430, 438. The shaft is retracted in this way by rotating it relative to the sleeve 418.

The threaded shaft 422 is then advanced through the sleeve 418 by rotating it relative to the shaft to drive the end wall 428 of the shaft into contact with the bearing surface 404 of the head part 400. This leads to surface to surface contact between the assembly surface 408 of the head part and the end wall 438 of the second end of the arm. The head part becomes centered on the end wall as the circular seating member becomes seated on the bearing surface of the head part by translating across the U-seating member due to the action of the circular seating member against the bearing surface. The first axis $X_1$ which is defined by the bore 406 in the head part is then coincident with the second axis $X_2$ which is defined by the sleeve 418.

An impaction force can be applied to the head part to achieve a secure connection between it and the stem part through the shaft 322. An impaction force that is directed through the threaded shaft 412 is therefore coincident with the first axis $X_1$ that is defined by the bore in the head part. This ensures that when an impaction force is applied along the second axis $X_2$ the force is directed along the first axis $X_1$.

An impaction force can be applied to the head part through an impaction shaft which is inserted through the bore 423 in the threaded shaft 422. The longitudinal axis of the bore in the threaded shaft is coincident with the second axis $X_2$ as defined by sleeve 418. In turn the second axis $X_2$ is coincident with the first axis $X_1$ defined by the bore 406 in the head part. This helps to ensure that the impaction force is directed along the first axis $X_1$.

Figure 17A:
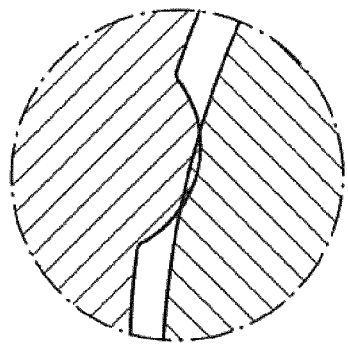
FIGS. 17a and 17b shows cross-sectional views through the longitudinal axis of the assembly shown in FIGS. 16a and 16b.
Figure 17A:
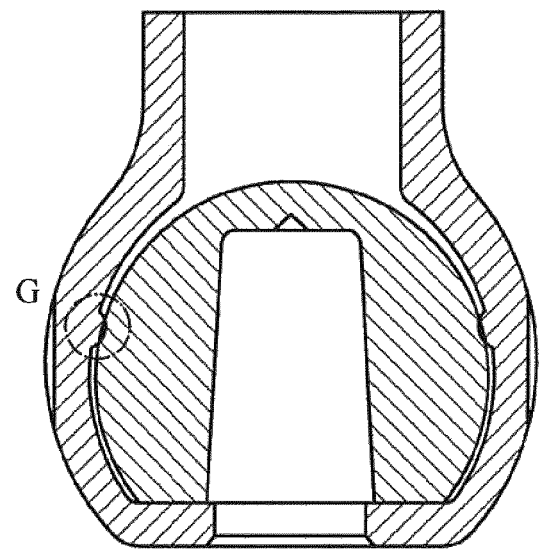
Figure 17B:
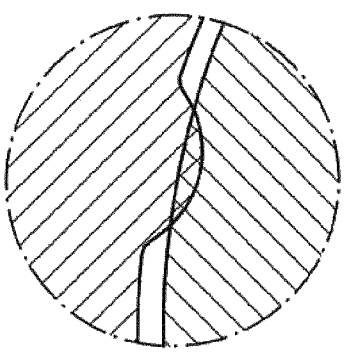
Figure 17B:
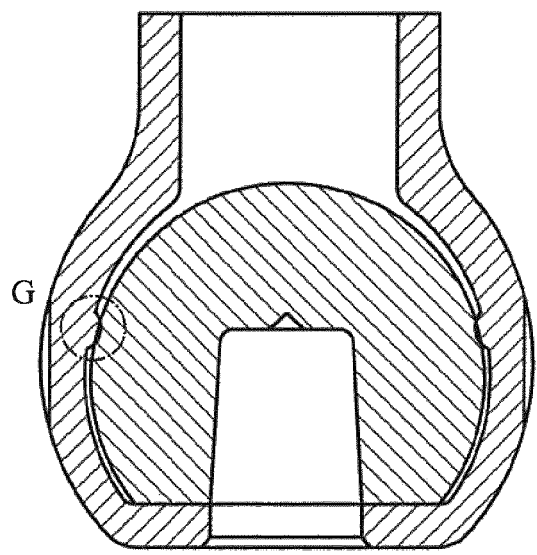
Figure 18:
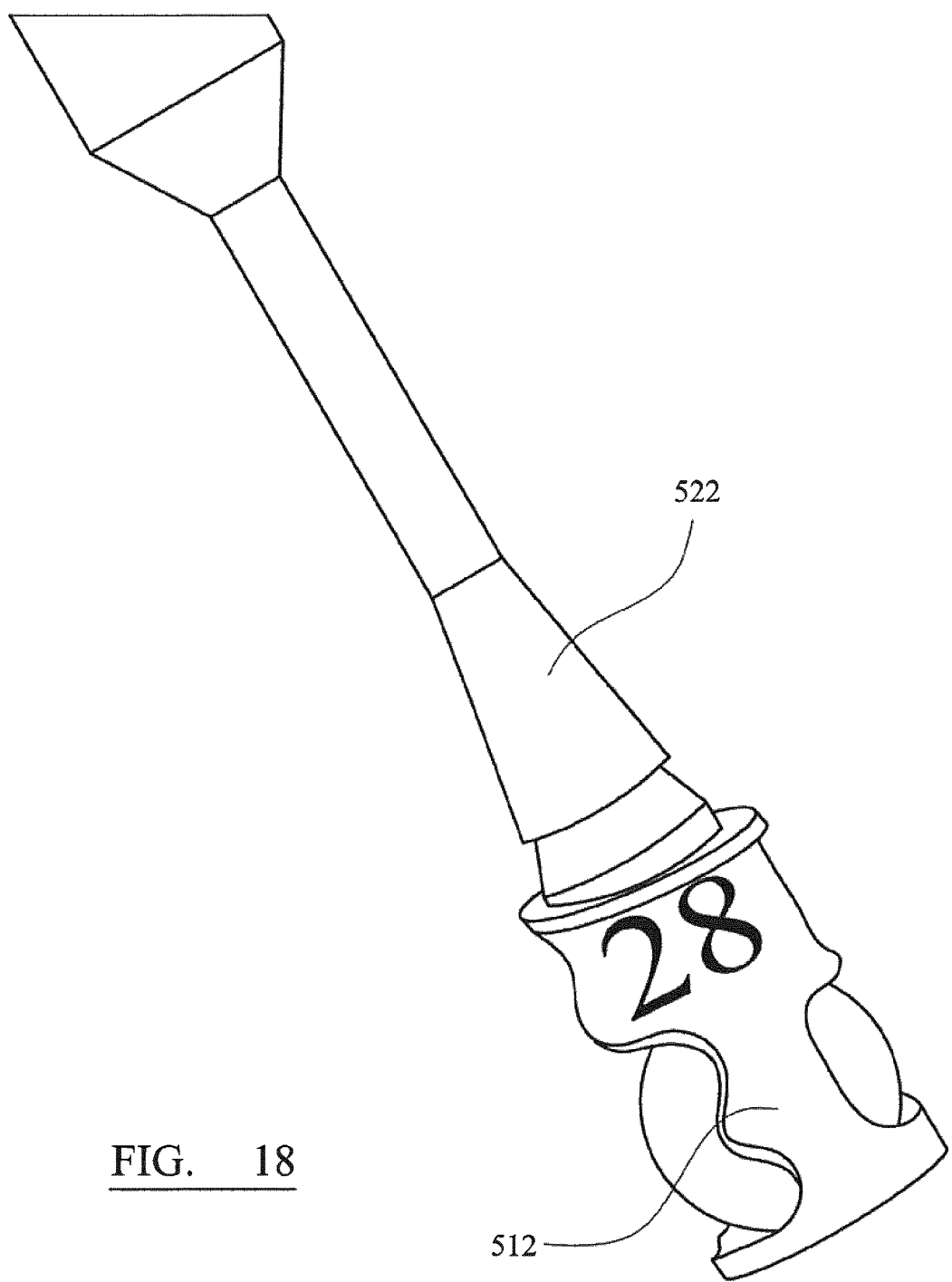
FIG. 18 is an isometric view of the assembly shown in FIG. 16 with an impaction rod inserted into the alignment guide.

FIGS. 16 to 18 show an orthopaedic joint prosthesis assembly which includes a head part 500 of a femoral component such as that shown in FIG. 2 and an alignment guide 510 for use in assembling the stem and head parts of a femoral component. The assembly has features in common with the assembly which is discussed above with reference to FIGS. 14 and 15. The head part 500 of the femoral component can be fitted to a stem part having a tapered spigot at its proximal end. The head part 500 has a bearing surface 504 and a bore 506 in an assembly surface 508. The assembly surface includes a chamfer portion 508*a*.

The alignment guide 510 includes an axial portion in the form of a plain bore sleeve 518 having a longitudinal axis $X_2$. First and second arms 512, 514 extend from the distal portion of the sleeve 518 such that a space is formed between each arm. The inner surface of each arm has a contact surface, the shape of which substantially corresponds to that of the bearing surface of the head part of an orthopaedic joint prosthesis. This facilitates a nesting fit between the bearing surface of the head part and the contact surface of each arm. When the bearing surface of the head is convex, the contact surface of each arm can be concave. As shown in FIGS. 16*b* and 16*c*, retention pinch points, can be provided on the contact surface of each of the first and second arms 512, 514. The retention pinch points are preferably located at or above the equator of the femoral head component. The retention pinch points aid in the stable retention of the femoral head component within the alignment guide and also apply a force to push the femoral head component downwardly towards the assembly surface seating member. The retention pinch points can take the form of an inwardly protruding rib 524*a*, 524*b* (as shown in FIG. 16*a*) or an angled straight face 526*a*, 526*b* (as shown in FIG. 16*c*).

Figure 16A:
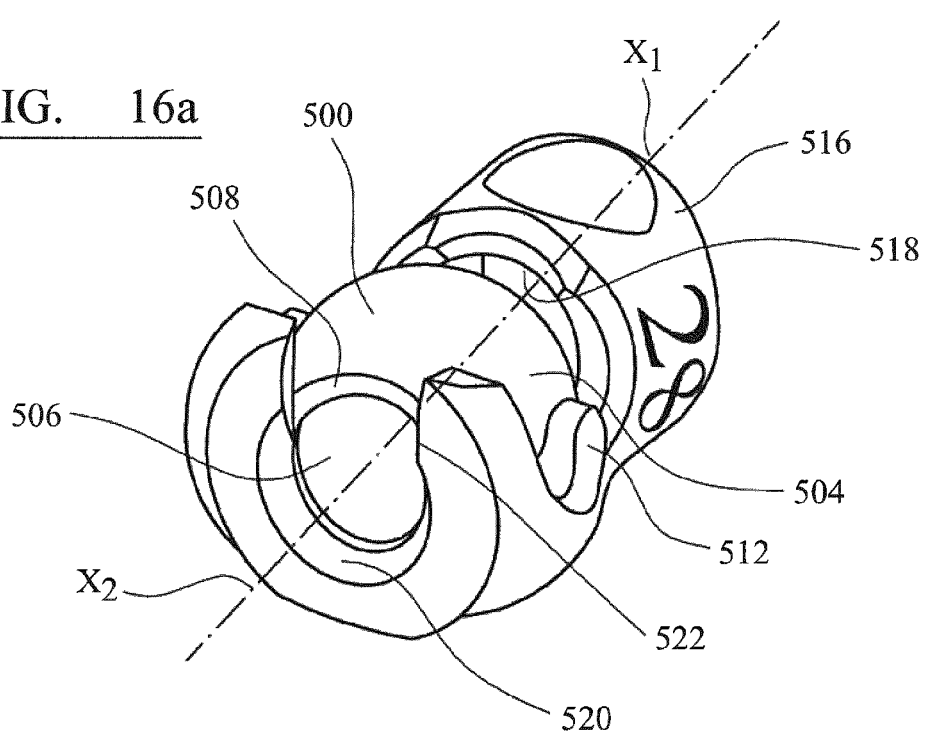
FIGS. 16a to 16c show isometric views of another orthopaedic joint prosthesis assembly comprising a modular femoral component of a hip joint prosthesis and the alignment guide.
Figure 16B:
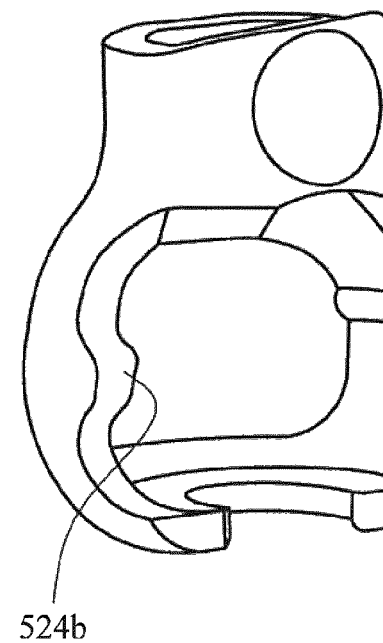
Figure 16C:
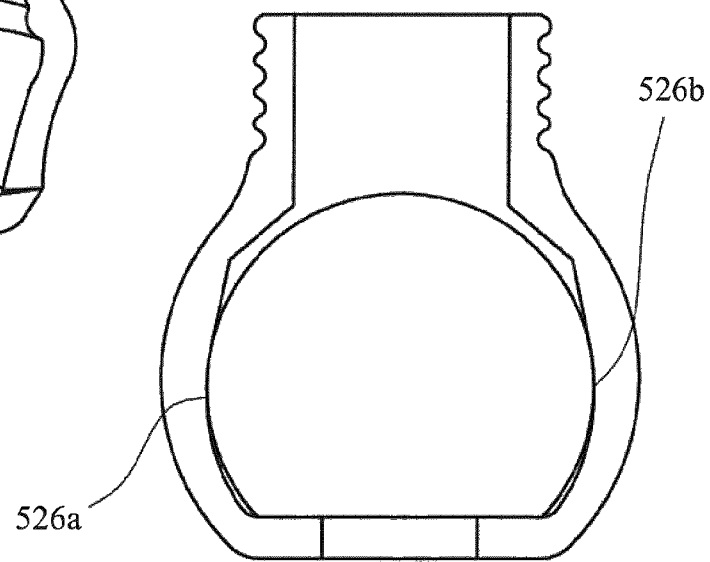

FIGS. 17*a* and 17*b* show cross sectional views of the assembly shown in FIG. 16*a* taken along the longitudinal axis $X_2$. FIG. 17*a* shows the retention of a 36 mm femoral head with a −2.0 offset retained within the alignment guide. FIG. 17*b* shows the retention of a 36 mm femoral head with a +8.5 offset retained within the same alignment guide. The ability of the same alignment guide to retain femoral heads with different offsets is achieved by the provision of the retentions pinch point 524*a*, 524*b*.

Each arm 512, 514 has a proximal end 516 and a distal end 520. The distal end of each arm joins to form a U-shaped bracket 522. The U-shaped bracket carries a U-shaped assembly surface seating member which is also U-shaped. The space between the arms of the seating member is at least equal to the diameter of the bore 506. The surface of the seating member which contacts the assembly surface is smooth. The alignment guide is made from a polymeric material by for example moulding or machining. The material is capable of resilient deformation.

The alignment guide can be provided in a range of sizes, each size of guide being specific for a particular size of head part. For example, the alignment guide shown is configured for use with a 28 mm diameter femoral head. In some constructions, the head part is mounted within, and packaged with the alignment guide. This is particularly advantageous because it minimizes the amount of handling of the head part prior to implantation. This reduces the risk of a breach of sterility of the head part and any damage to the bearing surface.

As shown in FIG. 16*a*, the head part 500 of a femoral prosthesis component can be fitted into the alignment guide 510 by press-fitting the femoral head between the arms 512, 514. The resilient deformity of the material of the arms 512, 514 means that the head part is retained within the space defined between the arms. The head part is positioned such that there is surface to surface contact between the assembly surface 508 of the head part and the inner surface of the U-shaped assembly surface seating member. As shown in FIG. 18, an impaction force can be applied to the head part through an impaction shaft 522 which is inserted through the bore of the sleeve 518. The distal end of the impaction shaft is shaped to correspond to that of the bearing surface. When the bearing surface of the head is convex, the distal end of the impaction shaft can be concave. The distal end of the impaction shaft is brought into contact with the bearing surface and functions as a bearing surface seating member. The sleeve defines the orientation of the impaction shaft relative to the axis which is defined by the bore 506. The sleeve ensures that the longitudinal axis of the impaction shaft is coincident with the second axis $X_2$ of the sleeve. In turn, the second axis $X_2$ is coincident with the first axis $X_1$ which is defined by the bore in the head part. This ensures that when an impaction force is applied along the second axis $X_2$ the force is directed along the first axis $X_1$.

Figure 19:
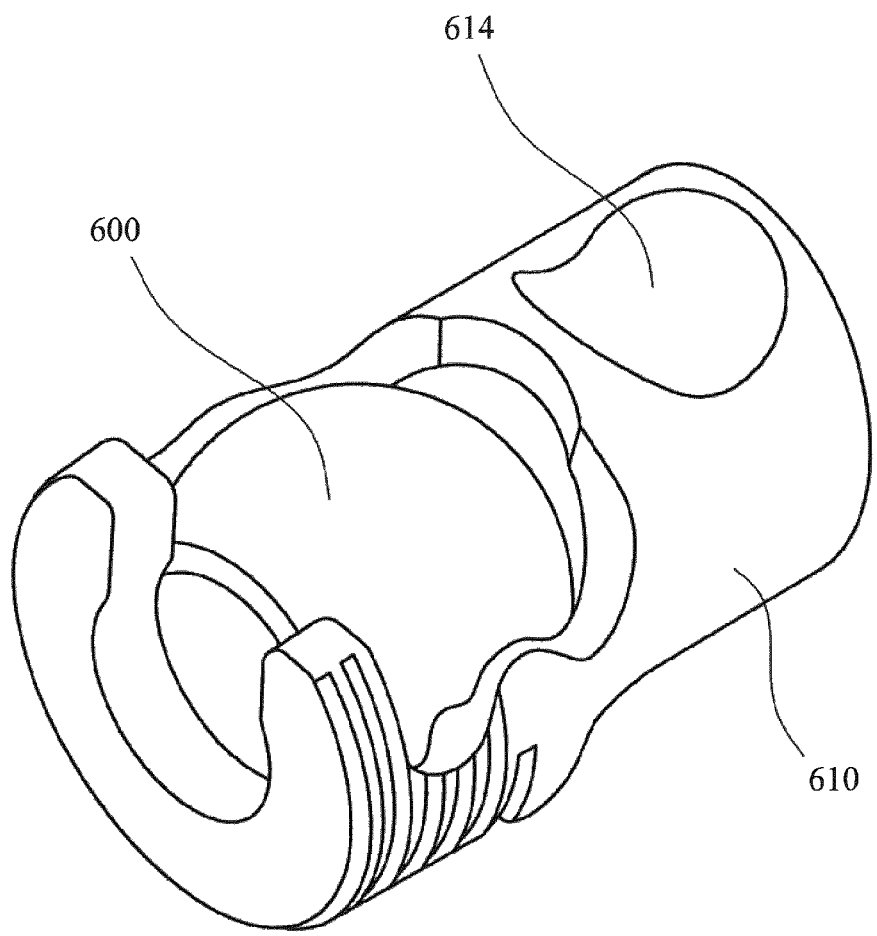
FIG. 19 is an isometric view of another orthopaedic joint prosthesis assembly comprising a modular femoral component of a hip joint prosthesis and the alignment guide.
Figure 20:
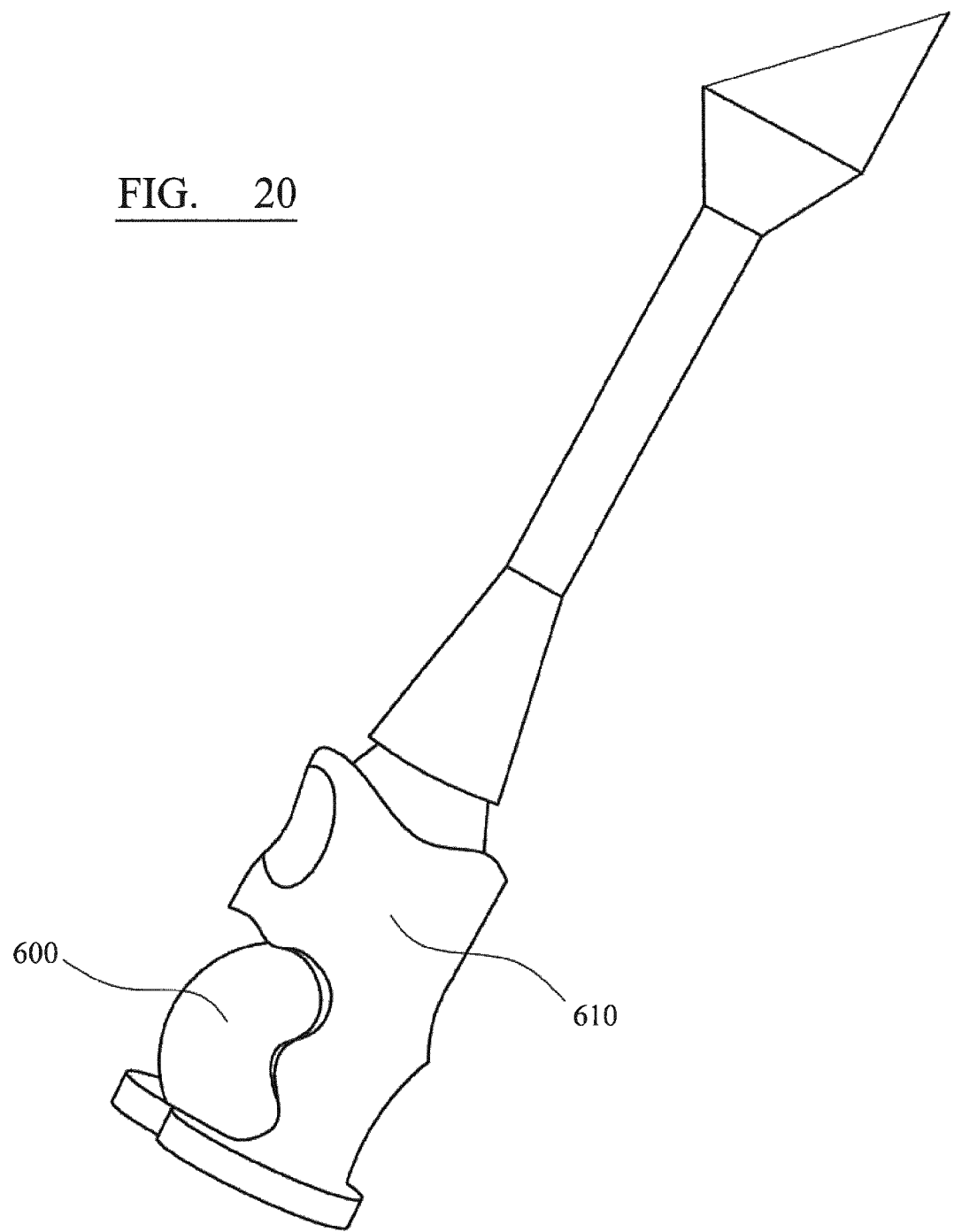
FIG. 20 is an isometric view of the assembly shown in FIG. 19 with an impaction rod inserted into the alignment guide.

FIGS. 19 and 20 show an orthopaedic joint prosthesis assembly which includes a head part 600 of a femoral component such as that shown in FIG. 2 and an alignment guide 610 for use in assembling the stem and head parts of a femoral component. The assembly has features in common with the assembly which is discussed above with reference to FIGS. 16 and 17. The outer surface of the distal portion of each arm is provided with a series of grooves which aid in the handling of the alignment guide. A depression 614 is provided on the outer surface of the sleeve. The depression 614 is dimensioned for receipt of a user's thumb. This also improves the handling of the alignment guide.

Figure 21:
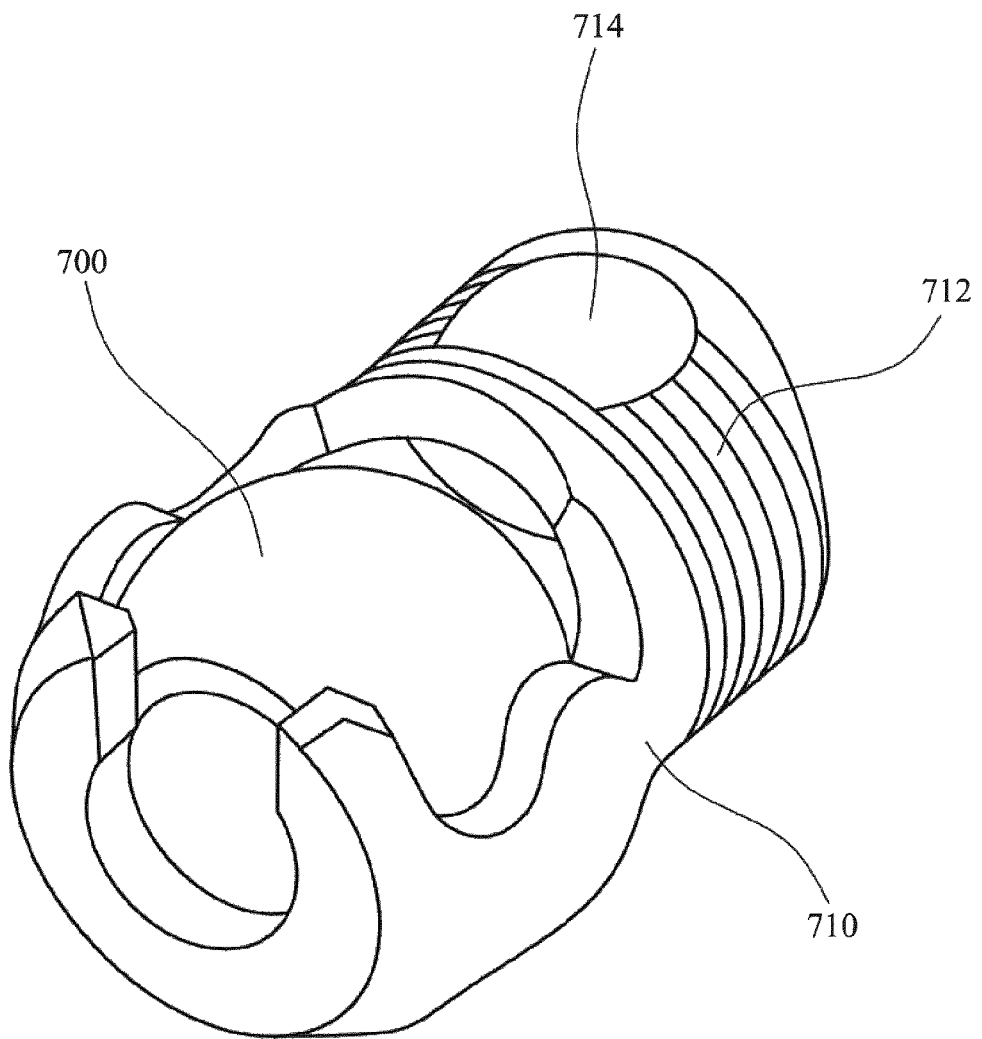
FIG. 21 is an isometric view of another orthopaedic joint prosthesis assembly comprising a modular femoral component of a hip joint prosthesis and the alignment guide.
Figure 22:
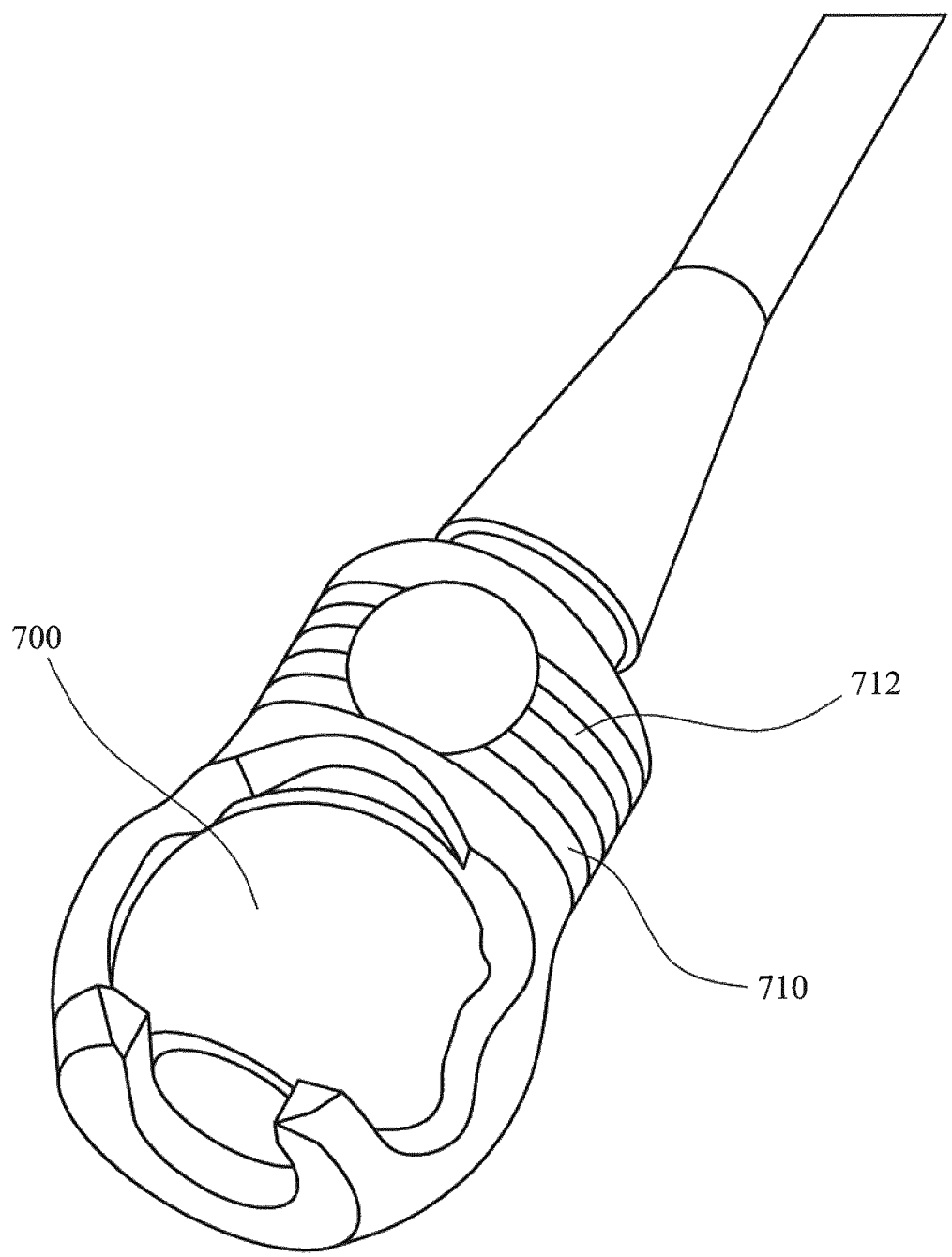
FIG. 22 is an isometric view of the assembly shown in FIG. 21 with an impaction rod inserted into the alignment guide.

FIGS. 21 and 22 show an orthopaedic joint prosthesis assembly which includes a head part 700 of a femoral component such as that shown in FIG. 2 and an alignment guide 710 for use in assembling the stem and head parts of a femoral component. The assembly has features in common with the assembly which is discussed above with reference to FIGS. 16 and 17. The sleeve 712 is provided with circumferentially arranged grooves on the outer surface. The grooves aid in the handling of the alignment guide. A depression 714 is provided on the outer surface of the sleeve. The depression is dimensioned for receipt of a user's thumb. This also improves the handling of the alignment guide.

The assembly surface seating member which engages the assembly surface of the head part can be essentially planar as discussed above in relation to at least some of the devices shown in the drawings. The assembly surface seating member could be formed with at least one formation defining at least part of a circle, which can engage the assembly surface around at least part of the periphery of the head part. The formation might be U-shaped so that its shape matches that of the seating member, with the base of the "U" being shaped as a part (especially about half) of a circle. The assembly surface seating member can be formed with a series of formations (for example at least two or at least three or at least four) which can engage the assembly surfaces on head parts of different sizes. This can be appropriate in relation to the devices shown in FIGS. 10 and 11, FIGS. 12 and 13, and FIGS. 14 and 15.

We claim:

1. An orthopaedic joint prosthesis assembly which comprises:
   a. a head part of an orthopaedic joint prosthesis component, which has a spherical bearing surface for articulation with a corresponding joint surface, and an assembly surface having a first bore formed in it for receiving a spigot on another part of the orthopaedic joint prosthesis, said bore having a first axis that extends perpendicular to the assembly surface, and in which there is a discontinuity at an interface between the bearing surface and the assembly surface, the said assembly surface being arranged on a plane which is parallel to, or contains, a plane which is defined by the opening to the bore in the head part when the head part is viewed from one side in cross-section, and
   b. an alignment guide comprising an axial portion and an arm extending from the axial portion, the arm including a distal portion and a proximal portion, the distal portion being configured to engage the assembly surface of the head part, the axial portion defining a second axis and being arranged to engage the bearing surface of the head part, directly or indirectly, when the head part is mounted within the guide, with the second axis coincident with the first axis, such that when an impaction force is applied along the second axis the force is directed along the first axis;
   wherein the alignment guide includes at least two arms and in which the distal portion of each arm includes an in-turned lip; and
   wherein at least one of the arms is capable of being pivoted relative to the other arm to provide access for mounting the head part within the alignment guide.

2. The alignment guide as claimed in claim 1, in which the guide further comprises a bearing surface seating member.

3. The alignment guide as claimed in claim 2, in which the bearing surface seating member has a contact surface which is concave so that it is configured to contact the bearing surface of a prosthesis component head part which is convex.

4. The alignment guide as claimed in claim 1, in which alignment guide includes a shaft through which an impaction force can be applied through the hearing surface seating member to a prosthesis component head part mounted within the alignment guide, and in which the shaft is mounted in the axial portion so that its axis is coincident with the second axis defined by the axial portion.

5. The alignment guide as claimed in claim 4, in which the axial portion includes a sleeve and the shaft is able to translate within the sleeve along the axis defined by the sleeve.

6. The alignment guide as claimed in claim 5, in which the sleeve and the shaft have cooperating threads so that the shaft can be advanced through the sleeve by rotating it about its axis.

7. The alignment guide as claimed in claim 4, in which the axial portion includes a hub spar having a socket and the shaft is able to translate within the socket along the axis defined by the socket.

8. The alignment guide as claimed in claim 7, in which the hub spar includes a feature defining the location of the hearing surface seating member, the bub spar having a concave inner surface defining a space in which a head part can be received.

9. The alignment guide as claimed in claim 8, in which the huh spar includes first and second arms which are connected to the hub spar at its widest point so that they can be pivoted relative to the huh spar between a retracted position which allows a head part to be mounted within the said space and a deployed position in which ahead part position in the said space is retained therein.

10. The assembly as claimed in claim 1, which includes a part of the orthopaedic joint prosthesis having a spigot which can be received in the bore in the assembly surface of the head part.

11. The assembly as claimed in claim 1, which the assembly surface includes a chamber portion extending around the head part, inclined to the plane which is defined by the opening to the bore in the head part.

* * * * *